(12) United States Patent
Rothberg et al.

(10) Patent No.: US 9,592,032 B2
(45) Date of Patent: Mar. 14, 2017

(54) ULTRASONIC IMAGING COMPRESSION METHODS AND APPARATUS

(71) Applicant: Butterfly Network, Inc., Guilford, CT (US)

(72) Inventors: Jonathan M. Rothberg, Guilford, CT (US); Tyler S. Ralston, Clinton, CT (US); Nevada J. Sanchez, Guilford, CT (US); Andrew J. Casper, Clinton, CT (US)

(73) Assignee: Butterfly Network, Inc., Guilford, CT (US)

( * ) Notice: Subject to any disclaimer, the term of this patent is extended or adjusted under 35 U.S.C. 154(b) by 0 days.

(21) Appl. No.: 14/689,080

(22) Filed: Apr. 17, 2015

(65) Prior Publication Data

US 2015/0297193 A1 Oct. 22, 2015

Related U.S. Application Data

(60) Provisional application No. 61/981,491, filed on Apr. 18, 2014.

(51) Int. Cl.
*A61B 8/14* (2006.01)
*A61B 8/00* (2006.01)
(Continued)

(52) U.S. Cl.
CPC .............. *A61B 8/56* (2013.01); *A61B 8/4483* (2013.01); *A61B 8/488* (2013.01); *A61B 8/5207* (2013.01);
(Continued)

(58) Field of Classification Search
CPC ............................ A61B 8/5207; G01A 7/5208
See application file for complete search history.

(56) References Cited

U.S. PATENT DOCUMENTS 4,594,662 A 6/1986 Devaney
5,269,307 A 12/1993 Fife et al.
(Continued)

FOREIGN PATENT DOCUMENTS

CN 102 981 156 A 3/2013
WO WO 2007/095499 A2 8/2007
(Continued)

OTHER PUBLICATIONS

Kim, Insoo. "Fully Integrated CMOS Ultrasound Transceiver Chip for High-Frequency High-Resolution Ultrasonic Imaging Systems", 2009, Pennsylvania State University, College of Engineering, pp. 1-157.*

(Continued)

*Primary Examiner* — James Kish
(74) *Attorney, Agent, or Firm* — Wolf, Greenfield & Sacks, P.C.

(57) ABSTRACT

To implement a single-chip ultrasonic imaging solution, on-chip signal processing may be employed in the receive signal path to reduce data bandwidth and an output data module may be used to move data for all received channels off-chip as a digital data stream. The digitization of received signals on-chip allows advanced digital signal processing to be performed on-chip, and thus permits the full integration of an entire ultrasonic imaging system on a single semiconductor substrate. The on-chip digitization of received signals also enables the on-chip integration of ultrasound processing and/or pre-processing to reduce the burden on off-chip computing. Data compression architectures are disclosed to facilitate the transfer of data off-chip as a digital data stream in accordance with the bandwidth requirements of standard commercially-available output interfaces.

24 Claims, 20 Drawing Sheets

(51) Int. Cl.
*A61B 8/08* (2006.01)
*G01S 7/52* (2006.01)
*G01S 15/89* (2006.01)

(52) U.S. Cl.
CPC ........ *G01S 7/5208* (2013.01); *G01S 7/52033* (2013.01); *G01S 7/52034* (2013.01); *G01S 15/8915* (2013.01)

(56) References Cited

U.S. PATENT DOCUMENTS

| | | | |
|---|---|---|---|
| 5,601,083 A * | 2/1997 | Anderson | G01S 7/6245 600/443 |
| 5,722,412 A * | 3/1998 | Pflugrath | A61B 8/00 600/441 |
| 5,740,805 A | 4/1998 | Dolazza et al. | |
| 5,782,769 A | 7/1998 | Hwang et al. | |
| 5,817,024 A | 10/1998 | Ogle et al. | |
| 5,893,363 A | 4/1999 | Little et al. | |
| 6,135,961 A | 10/2000 | Pflugrath et al. | |
| 6,203,498 B1 | 3/2001 | Bunce et al. | |
| D456,509 S | 4/2002 | Schultz | |
| 6,364,839 B1 | 4/2002 | Little et al. | |
| 6,371,918 B1 | 4/2002 | Bunce | |
| 6,383,139 B1 | 5/2002 | Hwang et al. | |
| 6,416,475 B1 | 7/2002 | Hwang et al. | |
| D461,895 S | 8/2002 | Barnes et al. | |
| 6,430,109 B1 | 8/2002 | Khuri-Yakub et al. | |
| 6,443,901 B1 | 9/2002 | Fraser | |
| 6,447,451 B1 | 9/2002 | Wing et al. | |
| 6,471,651 B1 | 10/2002 | Hwang et al. | |
| 6,569,101 B2 | 5/2003 | Quistgaard et al. | |
| 6,575,908 B2 | 6/2003 | Barnes et al. | |
| 6,604,630 B1 | 8/2003 | Cabatic et al. | |
| 6,632,178 B1 | 10/2003 | Fraser | |
| 6,645,145 B1 | 11/2003 | Dreschel et al. | |
| 6,648,826 B2 | 11/2003 | Little et al. | |
| 6,659,954 B2 | 12/2003 | Robinson | |
| 6,694,817 B2 | 2/2004 | Degertekin et al. | |
| 6,795,374 B2 | 9/2004 | Barnes et al. | |
| 6,831,294 B1 | 12/2004 | Nishimura et al. | |
| 6,831,394 B2 | 12/2004 | Baumgartner et al. | |
| 6,835,177 B2 | 12/2004 | Fritz et al. | |
| 6,865,140 B2 | 3/2005 | Thomenius et al. | |
| 6,880,137 B1 | 4/2005 | Burlison et al. | |
| 6,958,255 B2 | 10/2005 | Khuri-Yakub et al. | |
| 6,962,566 B2 | 11/2005 | Quistgaard et al. | |
| 6,974,417 B2 | 12/2005 | Lockwood et al. | |
| 7,030,536 B2 | 4/2006 | Smith et al. | |
| 7,037,746 B1 | 5/2006 | Smith et al. | |
| 7,052,464 B2 | 5/2006 | Wodnicki | |
| 7,125,383 B2 | 10/2006 | Hoctor et al. | |
| 7,257,051 B2 | 8/2007 | Thomenius et al. | |
| 7,280,435 B2 | 10/2007 | Thomenius et al. | |
| 7,285,897 B2 | 10/2007 | Fisher et al. | |
| 7,293,462 B2 | 11/2007 | Lee et al. | |
| D558,351 S | 12/2007 | Diener et al. | |
| 7,303,530 B2 | 12/2007 | Barnes et al. | |
| 7,313,053 B2 | 12/2007 | Wodnicki | |
| 7,353,056 B2 | 4/2008 | Hazard et al. | |
| 7,375,420 B2 | 5/2008 | Fisher et al. | |
| 7,408,283 B2 | 8/2008 | Smith et al. | |
| 7,425,199 B2 | 9/2008 | Hoctor et al. | |
| 7,441,321 B2 | 10/2008 | Baumgartner et al. | |
| 7,441,447 B2 | 10/2008 | Degertekin et al. | |
| 7,443,765 B2 | 10/2008 | Thomenius et al. | |
| 7,449,640 B2 | 11/2008 | Coleman | |
| 7,451,651 B2 | 11/2008 | Woychik et al. | |
| 7,470,232 B2 | 12/2008 | Hoctor et al. | |
| D591,423 S | 4/2009 | Diener et al. | |
| 7,530,952 B2 | 5/2009 | Huang et al. | |
| 7,534,211 B2 | 5/2009 | Hwang et al. | |
| 7,545,012 B2 | 6/2009 | Smith et al. | |
| 7,546,769 B2 | 6/2009 | Ramaswamy et al. | |
| 7,549,961 B1 | 6/2009 | Hwang | |
| 7,549,962 B2 | 6/2009 | Dreschel et al. | |
| 7,564,172 B1 | 7/2009 | Huang | |
| 7,604,596 B2 | 10/2009 | Hwang et al. | |
| 7,612,483 B2 | 11/2009 | Degertekin | |
| 7,612,635 B2 | 11/2009 | Huang | |
| 7,615,834 B2 | 11/2009 | Khuri-Yakub et al. | |
| 7,622,848 B2 | 11/2009 | Lee et al. | |
| 7,646,133 B2 | 1/2010 | Degertekin | |
| 7,686,766 B2 | 3/2010 | Quistgaard et al. | |
| 7,687,976 B2 | 3/2010 | Haider et al. | |
| 7,740,586 B2 | 6/2010 | Hwang et al. | |
| 7,745,248 B2 | 6/2010 | Park et al. | |
| 7,759,839 B2 | 7/2010 | Huang | |
| 7,764,003 B2 | 7/2010 | Huang | |
| 7,775,979 B2 | 8/2010 | Thomenius et al. | |
| 7,779,696 B2 | 8/2010 | Huang | |
| 7,809,400 B1 | 10/2010 | Hwang | |
| 7,819,807 B2 | 10/2010 | Barnes et al. | |
| 7,824,335 B2 | 11/2010 | Wodnicki | |
| 7,846,102 B2 | 12/2010 | Kupnik et al. | |
| 7,867,168 B2 | 1/2011 | Little et al. | |
| 7,878,977 B2 | 2/2011 | Mo et al. | |
| 7,880,565 B2 | 2/2011 | Huang | |
| 7,888,709 B2 | 2/2011 | Lemmerhirt et al. | |
| 7,892,176 B2 | 2/2011 | Wodnicki et al. | |
| 7,898,905 B2 | 3/2011 | Wodnicki et al. | |
| 7,952,260 B2 | 5/2011 | Haider et al. | |
| 7,954,387 B1 | 6/2011 | Furlong | |
| 7,955,264 B2 | 6/2011 | Mathew et al. | |
| 7,956,510 B2 | 6/2011 | Huang | |
| 7,978,461 B2 | 7/2011 | Diener et al. | |
| 7,996,688 B2 | 8/2011 | Little | |
| 8,004,373 B2 | 8/2011 | Huang | |
| 8,008,105 B2 | 8/2011 | Huang | |
| 8,008,835 B2 | 8/2011 | Degertekin | |
| 8,018,301 B2 | 9/2011 | Huang | |
| 8,038,620 B2 | 10/2011 | Lee et al. | |
| 8,052,606 B2 | 11/2011 | Barnes et al. | |
| 8,066,642 B1 | 11/2011 | Little et al. | |
| 8,105,941 B2 | 1/2012 | Huang | |
| 8,120,229 B2 | 2/2012 | Huang | |
| 8,128,050 B1 | 3/2012 | Sliger | |
| 8,133,182 B2 | 3/2012 | Wagner | |
| 8,137,278 B2 | 3/2012 | Lundberg et al. | |
| D657,361 S | 4/2012 | Goodwin et al. | |
| 8,176,787 B2 | 5/2012 | Haider et al. | |
| 8,199,685 B2 | 6/2012 | Hwang | |
| 8,203,912 B2 | 6/2012 | Roest et al. | |
| 8,213,467 B2 | 7/2012 | Little et al. | |
| 8,216,146 B2 | 7/2012 | Hwang et al. | |
| 8,222,065 B1 | 7/2012 | Smeys et al. | |
| 8,226,563 B2 | 7/2012 | Petersen et al. | |
| 8,237,601 B2 | 8/2012 | Dunbar et al. | |
| 8,242,665 B2 | 8/2012 | Robinson et al. | |
| 8,247,945 B2 | 8/2012 | Huang | |
| 8,298,144 B2 | 10/2012 | Burcher | |
| 8,309,428 B2 | 11/2012 | Lemmerhirt et al. | |
| 8,315,125 B2 | 11/2012 | Lemmerhirt et al. | |
| 8,327,521 B2 | 12/2012 | Dirksen et al. | |
| 8,345,508 B2 | 1/2013 | Wodnicki et al. | |
| 8,345,513 B2 | 1/2013 | Huang | |
| 8,355,554 B2 | 1/2013 | Ma et al. | |
| 8,363,514 B2 | 1/2013 | Huang | |
| 8,372,011 B2 | 2/2013 | Degertekin | |
| 8,388,544 B2 | 3/2013 | Hoctor et al. | |
| 8,398,408 B1 | 3/2013 | Hansen et al. | |
| 8,398,554 B2 | 3/2013 | Degertekin | |
| 8,399,278 B2 | 3/2013 | Lemmerhirt et al. | |
| 8,402,831 B2 | 3/2013 | Kupnik et al. | |
| 8,409,095 B1 | 4/2013 | Marquis | |
| 8,429,808 B2 | 4/2013 | Huang | |
| 8,439,840 B1 | 5/2013 | Duffy | |
| 8,451,693 B2 | 5/2013 | Nikoozadeh et al. | |
| 8,461,978 B2 | 6/2013 | Garner et al. | |
| 8,483,014 B2 | 7/2013 | Huang | |
| 8,526,271 B2 | 9/2013 | Huang | |
| 8,527,033 B1 | 9/2013 | Williams et al. | |
| 8,559,274 B2 | 10/2013 | Huang | |
| 8,563,345 B2 | 10/2013 | Adler et al. | |

(56) References Cited

U.S. PATENT DOCUMENTS

| | | | |
|---|---|---|---|
| 8,647,279 B2 | 2/2014 | Daft et al. | |
| 8,658,453 B2 | 2/2014 | Lemmerhirt et al. | |
| 8,672,850 B1 | 3/2014 | Miller | |
| 8,689,606 B2 | 4/2014 | Schellekens et al. | |
| 8,804,457 B2 | 8/2014 | Franchini et al. | |
| 9,327,142 B2 | 5/2016 | Rothberg et al. | |
| 9,351,706 B2 | 5/2016 | Rothberg et al. | |
| 2002/0177774 A1 | 11/2002 | Hwang et al. | |
| 2003/0114760 A1 | 6/2003 | Robinson | |
| 2003/0139664 A1* | 7/2003 | Hunt | A61B 8/00 600/407 |
| 2005/0148840 A1 | 7/2005 | Lazenby | |
| 2005/0171431 A1 | 8/2005 | Petersen | |
| 2005/0177045 A1 | 8/2005 | Degertekin et al. | |
| 2005/0240127 A1 | 10/2005 | Seip et al. | |
| 2007/0239019 A1 | 10/2007 | Richard et al. | |
| 2007/0242567 A1 | 10/2007 | Daft et al. | |
| 2007/0276238 A1 | 11/2007 | Sudol | |
| 2008/0194053 A1 | 8/2008 | Huang | |
| 2008/0290756 A1 | 11/2008 | Huang | |
| 2008/0296708 A1 | 12/2008 | Wodnicki et al. | |
| 2009/0134497 A1 | 5/2009 | Barth et al. | |
| 2009/0142872 A1 | 6/2009 | Park et al. | |
| 2009/0250729 A1 | 10/2009 | Lemmerhirt et al. | |
| 2010/0063397 A1 | 3/2010 | Wagner | |
| 2010/0152587 A1 | 6/2010 | Haider et al. | |
| 2010/0191894 A1 | 7/2010 | Bartley et al. | |
| 2010/0225200 A1 | 9/2010 | Kupnik et al. | |
| 2010/0256488 A1 | 10/2010 | Kim et al. | |
| 2010/0315272 A1* | 12/2010 | Steele | G01D 3/032 341/110 |
| 2010/0317972 A1 | 12/2010 | Baumgartner et al. | |
| 2011/0060225 A1 | 3/2011 | Cogan et al. | |
| 2011/0071397 A1 | 3/2011 | Wodnicki et al. | |
| 2011/0084570 A1 | 4/2011 | Soeda et al. | |
| 2011/0218436 A1 | 9/2011 | Dewey et al. | |
| 2011/0272693 A1 | 11/2011 | Kobayashi et al. | |
| 2012/0022379 A1 | 1/2012 | Gubbini et al. | |
| 2012/0074509 A1 | 3/2012 | Berg et al. | |
| 2012/0289829 A1 | 11/2012 | Barnes et al. | |
| 2013/0116561 A1 | 5/2013 | Rothberg et al. | |
| 2013/0314260 A1 | 11/2013 | Gemmeke et al. | |
| 2014/0066763 A2 | 3/2014 | Rothberg et al. | |
| 2014/0217478 A1 | 8/2014 | Rothberg et al. | |
| 2014/0219062 A1 | 8/2014 | Rothberg et al. | |
| 2014/0264660 A1 | 9/2014 | Rothberg et al. | |
| 2014/0288428 A1 | 9/2014 | Rothberg et al. | |
| 2015/0032002 A1 | 1/2015 | Rothberg et al. | |
| 2015/0080724 A1 | 3/2015 | Rothberg et al. | |
| 2015/0087977 A1 | 3/2015 | Rothberg et al. | |
| 2015/0257733 A1* | 9/2015 | Corbett, III | A61B 8/4455 600/440 |
| 2016/0069989 A1 | 3/2016 | Rothberg et al. | |
| 2016/0202349 A1 | 7/2016 | Rothberg et al. | |

FOREIGN PATENT DOCUMENTS

| | | |
|---|---|---|
| WO | WO 2007/096636 A1 | 8/2007 |
| WO | WO 2012/017978 A2 | 2/2012 |
| WO | WO 2014/151362 A2 | 9/2014 |

OTHER PUBLICATIONS

International Preliminary Report on Patentability mailed Sep. 24, 2015 for Application No. PCT/US2014/025567.
Invitation to Pay Additional Fees mailed Jul. 2, 2014 for Application No. PCT/US2014/025567.
International Search Report and Written Opinion mailed Sep. 15, 2014 for Application No. PCT/US2014/025567.
Invitation to Pay Additional Fees mailed Nov. 26, 2014 for Application No. PCT/US2014/047553.
International Search Report and Written Opinion mailed Mar. 2, 2015 for Application No. PCT/US2014/047553.
Office Communication and Interview Summary mailed Mar. 26, 2015 for U.S. Appl. No. 14/561,328.
Office Communication mailed Mar. 16, 2015 for U.S. Appl. No. 14/561,504.
Interview Summary mailed Apr. 6, 2015 for U.S. Appl. No. 14/561,504.
[No Author Listed], Technical Publications: Vscan Version 1.x.x CE0470 User manual GM092102. Revision 05. GE Healthcare. 2011. Chapters 1-5. 81 pages.
[No Author Listed], Universal Series Bus 3.0 Specification. Revision 1.0. Hewlett-Packard Company, Intel Corporation, Microsoft Corporation, NEC Corporation, STEricsson, and Texas Instruments. Jun. 6, 2011. 531 pages.
Agarwal et al., Single-Chip Solution for Ultrasound Imaging Systems: Initial Results. 2007 IEEE Ultrasonics Symposium. Oct. 1, 2007;1563-6.
Bavaro et al., Element Shape Design of 2-D CMUT Arrays for Reducing Grating Lobes. IEEE Trans Ultrason Ferroelectr Freq Contr. Feb. 2008;55(2):308-18.
Calmes et al., Highly Integrated 2-D Capacitive Micromachined Ultrasonic Transducers. 1999 IEEE Ultrason Symp. 1999;1163-6.
Chen et al., Ultrasonic Imaging Front-End Design for CMUT: A 3-Level 30Vpp Pulse-Shaping Pulser with Improved Efficiency and a Noise-Optimized Receiver. IEEE Asian Solid-State Circuits Conference. Nov. 12-14, 2012;173-6.
Cheng et al., An Efficient Electrical Addressing Method Using Through-Wafer Vias for Two-Dimensional Ultrasonic Arrays. 2000 IEEE Ultrasonics Symposium. 2000;2:1179-82.
Cheng et al., CMUT-in-CMOS ultrasonic transducer arrays with on-chip electronics. Transducers 2009. IEEE. Jun. 21, 2009;1222-5.
Cheng et al., Electrical Through-Wafer Interconnects with Sub-PicoFarad Parasitic Capacitance. 2001 Microelectromechan Syst Conf. Aug. 24, 2001;18-21.
Daft et al., 5F-3 a Matrix Transducer Design with Improved Image Quality and Acquisition Rate. 2007 IEEE Ultrasonics Symposium. Oct. 1, 2007;411-5.
Daft et al., Microfabricated Ultrasonic Transducers Monolithically Integrated with High Voltage Electronics. 2004 IEEE Ultrasonics Symposium. Aug. 23, 2004;1:493-6.
Doody et al., Modeling and Characterization of CMOS-Fabricated Capacitive Micromachined Ultrasound Transducers. J Microelectromechan Sys. Feb. 2011;20(1):104-118.
Eccardt et al., Micromachined ultrasound transducers with improved coupling factors from a CMOS compatible process. Ultrasonics. Mar. 2000;38:774-80.
Eccardt et al., Surface micromachined ultrasound transducer in CMOS technology. Proc Ultrason Symp. 1996;959-62.
Gurun et al., Front-end CMOS electronics for monolithic integration with CMUT arrays: circuit design and initial experimental results. Proc Ultrason Symp. 2008;390-3.
Kim et al., Design and Test of a Fully Controllable 64×128 2-D CMUT Array Integrated with Reconfigurable Frontend ASICs for Volumetric Ultrasound Imaging. IEEE. International Ultrasonics Symposium Proceedings. Oct. 7-10, 2012;77-80. doi: 10.1109/ULTSYM.2012.0019.
Knight et al., Low Temperature Fabrication of Immersion Capacitive Micromachined Ultrasonic Transducers on Silicon and Dielectric Substrates. IEEE Trans Ultrason Ferroelectr Freq Contr. Oct. 2004;51(10):1324-33.
Kupnik et al., CMUT Fabrication Based on a Thick Buried Oxide Layer. Proc IEEE Ultrason Symp. Oct. 2010;2010:547-550. doi:10.1109/ULTSYM.2010.5935935. Epub Jun. 8, 2012. 10 pages.
Kupnik et al., Wafer-Bonded CMUT Meets CMOS. 2010 CMOS Emerging Technology Workshop. May 21, 2010;1-22.
Lin et al., Packaging of Large and Low-Pitch Size 2D Ultrasonic Transducer Arrays. MEMS Conf. 2010;508-11.
Nikoozadeh et al., Forward-Looking Intracardiac Ultrasound Imaging Using a 1-D CMUT Array Integrated With Custom Front-End Electronics. IEEE Trans Ultrason Ferroelectr Freq Contr. Dec. 2008;55(12):2651-60.
Noble et al., A cost-effective and manufacturable route to the fabrication of high-density 2D micromachined ultrasonic transducer

(56) References Cited

OTHER PUBLICATIONS arrays and (CMOS) signal conditioning electronics on the same silicon substrate. Proc Ultrason Symp. 2001;941-5.
Noble et al., Low-temperature micromachined CMUTs with fully-integrated analogue front-end electronics. Proc Ultrason Symp. 2002;1045-50.
Oralkan et al., Volumetric Imaging Using 2D Capacitive Micromachined Ultrasonic Transducer Arrays (CMUTs): Initial Results. 2002 IEEE Ultrason Symp. 2002;1083-6.
Oralkan et al., Volumetric Ultrasound Imaging Using 2-D CMUT Arrays. IEEE Trans Ultrason Ferroelectr Freq Contr. Nov. 2003;50(11):1581-94.
Park et al., Fabrication of Capacitive Micromachined Ultrasonic Transducers via Local Oxidation and Direct Wafer Bonding. J Microelectromechan Syst. Feb. 2011;20(1):95-103.
Tsuji et al., Low Temperature Process for CMUT Fabrication with Wafer Bonding Technique. IEEE Intl Ultrason Symp Proc. 2010;551-4.
Um et al., An Analog-Digital-Hybrid Single-Chip RX Beamformer with Non-Uniform Sampling for 2D-CMUT Ultrasound Imaging to Achieve Wide Dynamic Range of Delay and Small Chip Area. IEEE International Solid-State Circuits Conference. Feb. 12, 2014;426-8.
Wodnicki et al., Multi-Row Linear CMUT Array Using CMUTs and Multiplexing Electronics. Proc Ultrason Symp. 2009;2696-9.
Wolffenbuttel et al., Low-temperature silicon wafer-to-wafer bonding using gold at eutectic temperature. Sensors and Actuators A. 1994;43:223-9.
Wygant et al., Integration of 2D CMUT Arrays with Front-End Electronics for Volumetric Ultrasound Imaging. IEEE Trans Ultrason Ferroelectr Freq Contr. Feb. 2008;55(2):327-42.
Zahorian et al., Single chip CMUT arrays with integrated CMOS electronics: fabrication process development and experimental results. Proc Ultrason Symp. 2008;386-9.
Zhuang et al., Wafer-bonded 2-D CMUT arrays incorporating through-wafer trench-isolated interconnects with a supporting frame. IEEE Trans Ultrason Ferroelectr Freq Control. Jan. 2009;56(1):182-92. doi: 10.1109/TUFFC.2009.1018.
Interview Summary mailed May 7, 2015 for U.S. Appl. No. 14/561,328.
International Search Report and Written Opinion mailed Jul. 22, 2015 for Application No. PCT/US2015/026315.
International Preliminary Report on Patentability mailed Feb. 4, 2016 for Application No. PCT/US2014/047553.
International Preliminary Report on Patentability mailed Oct. 27, 2016 for Application No. PCT/US2015/026315.

\* cited by examiner

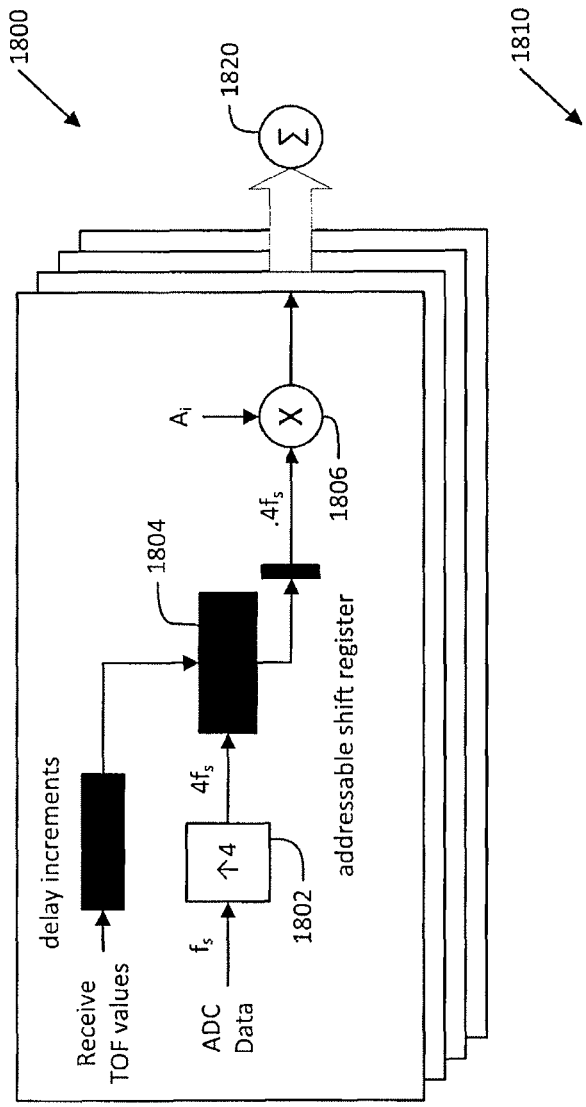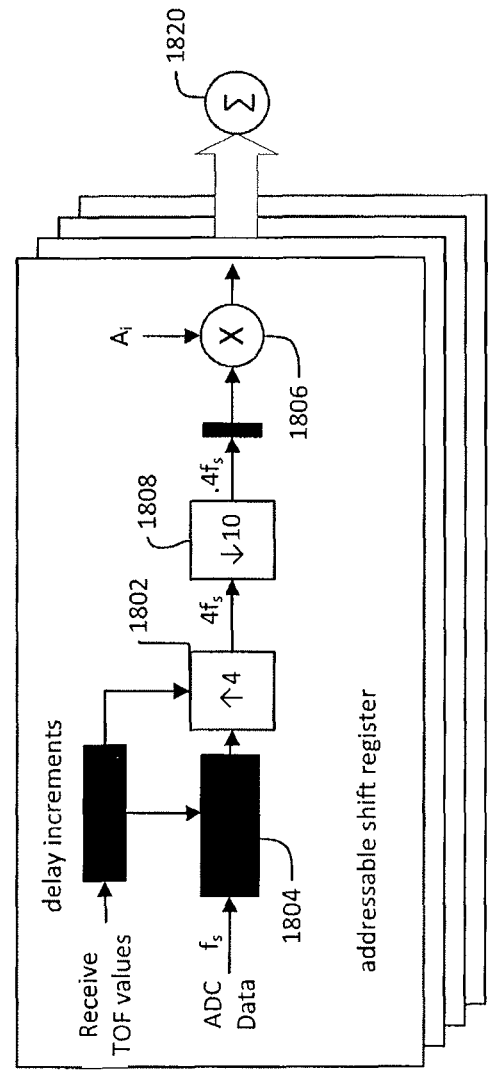
FIG. 18A
FIG. 18B

ULTRASONIC IMAGING COMPRESSION METHODS AND APPARATUS

CROSS-REFERENCE TO RELATED APPLICATIONS

The present application claims the benefit under 35 U.S.C. §119(e) of U.S. Provisional Patent Application Ser. No. 61/981,491 entitled "ULTRASONIC IMAGING COMPRESSION METHODS AND APPARATUS," filed Apr. 18, 2014, which is incorporated herein by reference in its entirety.

FIELD

Aspects of the present disclosure relate to ultrasonic imaging devices and methods.

BACKGROUND

Conventional ultrasonic scanners generally include discrete transducers and control electronics. The control electronics are typically not integrated with the transducers, but rather are formed and housed separately.

Ultrasound transducer probes used for medical applications typically produce a large amount of data, as needed to produce ultrasound images for medical applications. The higher the quality and complexity of images desired, the more data is typically needed. Typically, the data is transferred from the transducer probe to the separately housed control electronics using cabling.

SUMMARY

The present disclosure details various aspects of an architecture for on-chip compression of data acquired using an ultrasonic transducer-based imager. In some embodiments, on-chip signal processing (e.g., data compression) may be employed in the receive signal path, for example, to reduce data bandwidth. For example, some on-chip compression architectures described herein may be configured to compress full real-time 3D ultrasound imaging data to an extent that the compressed data may be transferred off-chip as a digital data stream using a consumer grade interface (e.g., USB 3.0, USB 3.1, USB 2.0, Thunderbolt, Firewire, etc.). The digitization of received signals on-chip allows advanced digital signal processing to be performed on-chip, and thus permits complete or substantially complete integration of an entire ultrasonic imaging system on a single semiconductor substrate. In some embodiments, a complete "ultrasound system on a chip" solution is provided.

Some embodiments are directed to a method for processing a signal output from an ultrasonic transducer element. The method comprises with a component integrated on a same semiconductor die as the ultrasonic transducer element, producing a compressed signal by compressing the signal output from the ultrasonic transducer element, wherein the compressed signal is configured to be transmitted out of the semiconductor die as a data stream.

Some embodiments are directed to a method, comprising performing on-chip compression of a plurality of ultrasound signals produced by an array of ultrasonic transducers integrated with the chip.

Some embodiments are directed to an ultrasound device, comprising at least one ultrasonic transducer element integrated on a semiconductor die; and a compression circuit, integrated on the semiconductor die, configured to compress a signal output from the at least one ultrasonic transducer element, wherein the compressed signal is configured to be transmitted out of the semiconductor die as a data stream.

Some embodiments are directed to an ultrasound device, comprising at least one ultrasonic transducer element integrated on a semiconductor die; and an image reconstruction circuit, integrated on the semiconductor die, configured to perform at least a portion of an image reconstruction process based, at least in part, on a signal output from the at least one ultrasonic transducer element.

Some embodiments are directed to a method, comprising performing at least a portion of an on-chip image reconstruction process based, at least in part, on a signal output from at least one ultrasonic transducer integrated with the chip.

Some embodiments are directed to a method for processing a signal output from an ultrasonic transducer element. The method comprises with a component integrated on a same semiconductor die as the ultrasonic transducer element, performing at least a portion of an image reconstruction process based at, least in part, on the signal output from the at least one ultrasonic transducer element.

Some embodiments are directed to an ultrasound device comprising at least one ultrasonic transducer element integrated on a semiconductor die and configured to generate an imaging signal; control circuitry configured to produce multiple imaging modes of operation of the ultrasound device; and compression circuitry, integrated on the semiconductor die, configured to compress the imaging signal utilizing one of a plurality of compression schemes, based, at least in part, on a selected imaging mode of operation.

Some embodiments are directed to a method for processing a signal output from at least one ultrasonic transducer element. The method comprises determining an imaging mode of operation of an ultrasound device comprising the at least one ultrasonic transducer element; and compressing data recorded by the ultrasound device using one of a plurality of compression schemes selected, based, at least in part, on the determined (e.g., programmed) imaging mode of operation.

It should be appreciated that all combinations of the foregoing concepts and additional concepts discussed in greater detail below (provided that such concepts are not mutually inconsistent) are contemplated as being part of the inventive subject matter disclosed herein.

BRIEF DESCRIPTION OF THE DRAWINGS

Various aspects and embodiments of the disclosed technology will be described with reference to the following figures. It should be appreciated that the figures are not necessarily drawn to scale. Items appearing in multiple figures are indicated by the same reference number in all the figures in which they appear.

FIGS. 18A and 18B show illustrative architectures for performing dynamic focusing using streaming addressable and pipeline delays, respectively, in accordance with some embodiments of the present disclosure.

DETAILED DESCRIPTION

Applicants have appreciated that the lack of integration of the transducers and control circuitry of conventional ultrasound scanners is demanded in part by the large amount of data collected by ultrasound transducer probes and used to generate ultrasound images. Correspondingly, Applicants have appreciated that suitable device configurations and techniques for reducing or otherwise handling such large amounts of data while still allowing for generation of desired ultrasound image types at suitable quality would facilitate the attainment of integrated ultrasound devices having ultrasonic transducers and control electronics in a compact form. The present disclosure addresses this issue by providing unique, cost-effective, and scalable integrated data compression architectures to reduce data bandwidth while providing data that is sufficiently robust for advanced imaging applications. Thus, aspects of the present application provide an architecture which may be used with a single substrate ultrasound device having integrated ultrasonic transducers (e.g., CMOS ultrasonic transducers) and circuitry.

Accordingly, some aspects of the present disclosure provide new apparatuses, systems, and methods that push the forefront of ultrasound image processing by providing a robust and highly integrated "ultrasound system on a chip" with direct integration of ultrasonic transducer arrays fabricated on the same die as a fully digital ultrasound front-end. As used herein, "fabricated/integrated on the same die" means integrated on the same substrate or integrated using one or more stacked die integrated with 3D chip packaging technology. According to some aspects of the present disclosure, these architectures may allow sufficient access to digitized channels that maintain independent data to permit the use of state-of-the-art, off-the-shelf computing platforms for performing sophisticated image formation and/or processing algorithms. In at least some embodiments, high-resolution 3D volumetric imaging, as just one example, may be performed using the devices and techniques for data reduction and handling described herein.

Figure 1A:
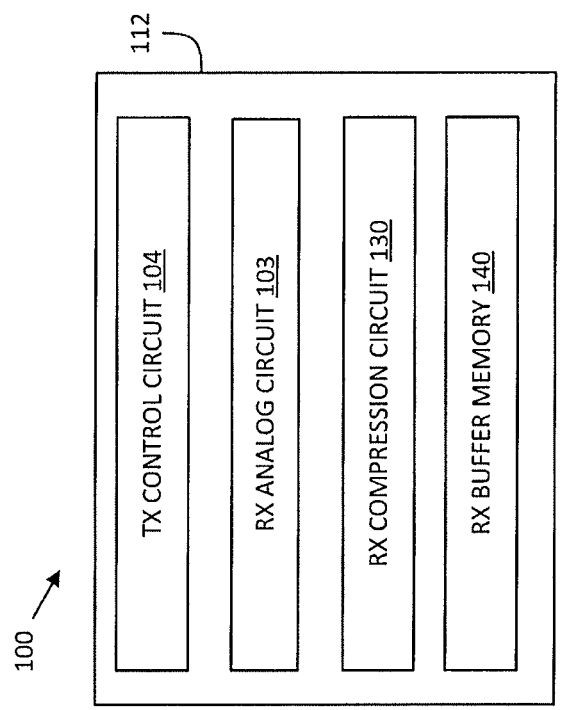
FIG. 1A shows an illustrative architecture block diagram of an ultrasonic imaging device in accordance with embodiments of the present disclosure.

FIG. 1A shows an illustrative example of an integrated ultrasound device 100 embodying various aspects of the present disclosure. As shown, the device 100 includes a plurality of circuits formed on a semiconductor die 112 including transmit (TX) control circuit 104, analog receive (RX) circuit 103, receive (RX) compression circuit 130, and receive (RX) buffer memory 140. Each of these circuits may include one or more additional circuits. For example, TX control circuit 104 may include TX waveform generators, TX parameter and control registers, analog pulsar circuitry to drive an array of acoustic elements and/or circuitry implementing a delayed waveform distribution function.

Figure 1B:
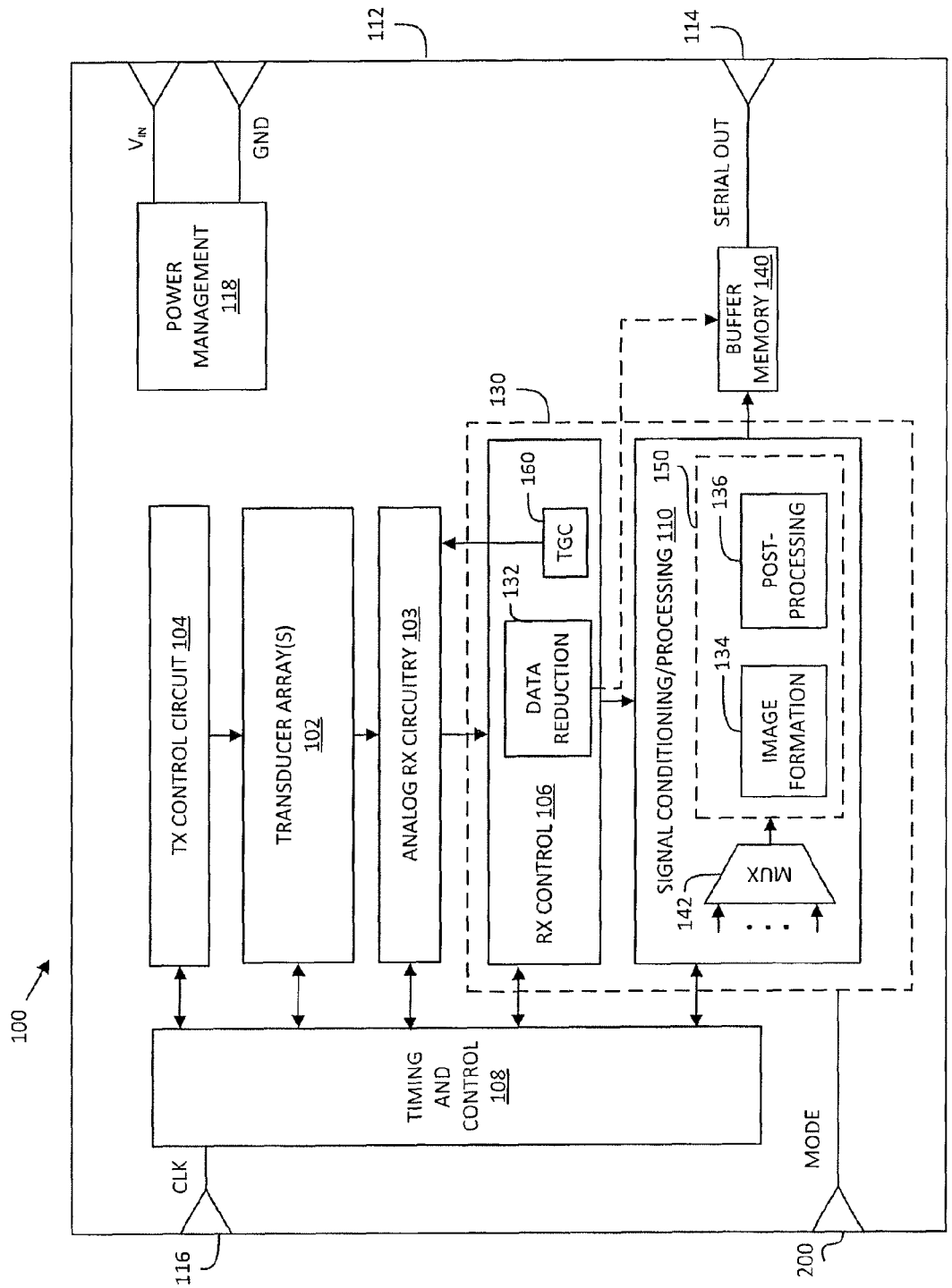
FIG. 1B shows the illustrative architecture of FIG. 1A when integrated with additional components, in accordance with some embodiments of the present disclosure.

FIG. 1B shows the ultrasound device 100 of FIG. 1A, including the elements shown in FIG. 1A with additional elements incorporated on semiconductor die 112. For example, device 100 in FIG. 1B additionally includes one or more transducer arrangements (e.g., arrays) 102, a timing & control circuit 108, and a power management circuit 118.

Analog RX circuit 103 may include analog signal chain components that process signals output from a plurality of ultrasonic transducer elements. The ultrasonic transducers of the ultrasonic transducer elements may be of any suitable type, and in some embodiments are capacitive micromachined ultrasound transducers (CMUTs), which may allow for fabrication of high quality ultrasonic transducers in the same semiconductor foundries that are currently driving the electronics industry. Such CMUTs may be formed in and/or formed on the same substrate as the integrated circuitry (e.g., a silicon substrate).

In one aspect, analog RX circuit 103 may include a plurality of rows (e.g., four rows). Each row may include analog signal chain elements (e.g., 144 elements) for a full column of sensors in an ultrasound transducer array. In some embodiments, one or more components (e.g., an automatic gain control component) in analog RX circuit 103 may be controlled by a time gain compensation (TGC) circuit 160 that compensates for signals received from different depths in an imaged object (e.g., by providing variable gain based on the timing at which the signal is received). TGC circuit 160 may be included as a portion of RX compression circuit 130 described below. An illustrative architecture for TGC circuit 160 is discussed in more detail below with respect to FIG. 4.

RX compression circuit 130 may include circuits for processing outputs from analog RX circuit 103. In some implementations, RX compression circuit 130 may include circuits configured to reduce a data bandwidth of data received from analog RX circuit 103, as discussed in more detail below. For example, RX compression circuit 130 may include circuits configured to process the received data by filtering, averaging, sampling, decimating, and/or using other techniques to provide on-chip compression to enable the processed data to be transmitted off-chip at a desired data rate. RX compression circuit 130 may include analog and/or digital components for performing data compression, and embodiments are not limited based on whether particular aspects of the compression circuitry is implemented using an analog architecture, a digital architecture, or using a combination of analog and digital components. For example, the digital mixing circuitry described in more detail below may alternatively be implemented using an analog heterodyning circuit to provide equivalent functionality. Additionally, other features including, but not limited to, channel summation, dynamic delay, and frequency filtering may be implemented using digital and/or analog components, and embodiments are not limited in this respect.

RX compression circuit 130 may also include other components including RX control and parameter registers. Additionally, RX compression circuit 130 may be associated with at least one microprocessor (not shown) integrated on die 112 that may be used, at least in part, to compress the digital signals processed by RX compression circuit 130.

RX buffer memory 140 may be configured to temporarily store the output of RX compression circuit 130 prior to transmitting the data off-chip, as discussed in further detail below.

Components included in some embodiments as a portion of RX compression circuit 130 are also shown. As discussed above, some embodiments of the present disclosure provide data compression architectures to facilitate the transfer of data off of semiconductor die 112 as a data stream at a data rate compatible with output interface 114 having a maximum data bandwidth. In some embodiments, the data stream may be a serial data stream. Components of RX compression circuit 130 (also referred to herein as "compression circuitry") may be configured to provide data compression using one or more data compression techniques, examples of which are described herein. RX compression circuit 130, as shown, includes an RX control circuit 106 and a signal conditioning/processing circuit 110. RX control circuit 106 further includes a data reduction circuit 132 configured to process data received from analog signal chain elements of analog RX circuitry 103. Data reduction circuit 132, discussed in more detail below, may include circuitry configured to perform data compression on signals prior to performing at least a portion of an image reconstruction process. In some embodiments, at least some outputs of data reduction circuit 132 may be provided to buffer memory 140 without being further processed by signal conditioning/processing circuit 110, as represented by the optional data path between data reduction circuit 132 and buffer memory 140.

In the example shown, data reduction circuit 132 may include analog compression circuitry, an analog-to-digital converter (ADC), and digital compression circuitry. The ADC may, for example, comprise a 10-bit, 1, 5, 10, or 20 mega-samples per second (Msps), 40 Msps, 50 Msps, or 80 Msps ADC. The ADC may alternatively have any desired resolution including, but not limited to, 1-bit, 4-bit, 16-bit, or 20-bit. Illustrative types of ADCs that may be used include, but are not limited to, a successive approximation register (SAR) ADC, a flash ADC, a pipeline ADC, a sigma-delta ADC, a multi-slop ADC, and a time-interleaved ADC. In some embodiments, the ADC may be sampling at a lower rate than the center frequency of the received signal, thereby aliasing relevant data.

After undergoing processing in the data reduction circuit 132, the outputs of all of the RX control circuits 106 (the number of which, in this example, is equal to or less than the number of transducer elements on the chip) may be transmitted to a multiplexer (MUX) 142 in the signal conditioning/processing circuit 110. In some embodiments, the number of RX control circuits may be different than the number of transducer elements on the chip, and embodiments of the present disclosure are not limited in this respect. The MUX 142 multiplexes the digital data from the various RX control circuits 106, and the output of the MUX 142 may optionally be provided to digital signal processing block 150 in the signal conditioning/processing circuit 110 prior to outputting the data from the die 112, e.g., via one or more output ports 114. Some embodiments may not include MUX 142, and outputs from the RX control circuits 106 may be provided directly to digital signal processing block 150 and/or stored in buffer 140 prior to being sent off the chip.

As shown, digital signal processing block 150 includes image formation circuit 134 configured to perform at least a portion of an image reconstruction process, and the output of the image formation circuit 134 may be output off-chip for further processing and/or display. Digital signal processing block 150 may also include post-processing circuit 136 that operates on the output of image formation circuit 134 to provide additional data compression. Illustrative architectures for each of data reduction circuit 132, image formation circuit 134, and post-processing circuit 136 that may be formed on a semiconductor die 112 as a portion of an ultrasound imager in accordance with embodiments of the present disclosure are discussed in more detail below. In some embodiments, discussed in more detail below, all or a portion of digital signal processing block 150 may be formed off-chip, and data from one or more RX control circuits 106 may be stored in buffer memory 140 without processing by signal conditioning and processing circuit 110.

As explained in more detail below, various components in RX compression circuit 130 may serve to decouple waveforms from the received signal and otherwise reduce the amount of data that is output from the die 112 via a data link or otherwise. The inclusion of such elements may thus further facilitate and/or enhance an "ultrasound-on-a-chip" solution in accordance with some embodiments.

In the embodiment shown in FIG. 1B, all of the illustrated components are formed on a single semiconductor die 112 or are formed on multiple stacked integrated dice using 3D packaging technology. It should be appreciated, however, that in alternative embodiments one or more of the illustrated elements may be instead located off-chip, as discussed in more detail below in connection with FIG. 3. In addition, although the illustrated example shows both a TX control circuit 101 and an RX control circuit 106, in alternative embodiments only a TX control circuit or only an RX control circuit may be employed. For example, such embodiments may be employed in a circumstance where one or more transmission-only devices 100 are used to transmit acoustic signals and one or more reception-only devices 100 are used to receive acoustic signals that have been transmitted through or reflected by a subject being ultrasonically imaged.

Figure 2:
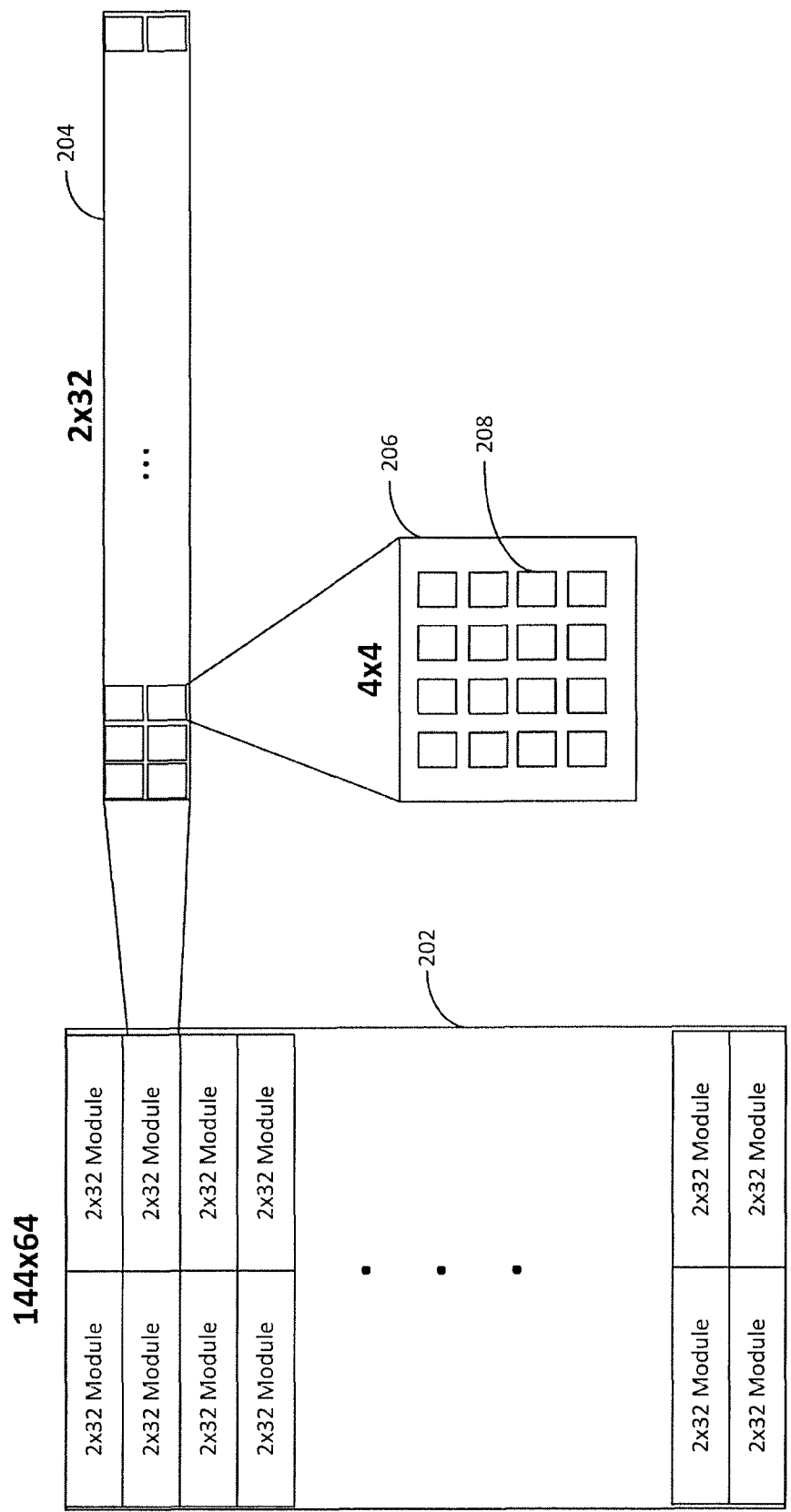
FIG. 2 shows a schematic illustration of the arrangement of individually-controllable modules of ultrasonic transducer elements in an array used in accordance with some embodiments of the present disclosure.

FIG. 2 shows an embodiment of ultrasound device 100 comprising a substrate 202 that includes multiple ultrasound circuitry modules 204 formed thereon. As shown, an ultrasound circuitry module 204 may comprise multiple ultrasound elements 206. An ultrasound element 206 may comprise multiple ultrasonic transducers 208. Such a modular design allows for scalability of the architecture to any desired size or arrangement.

In the illustrated embodiment, substrate 202 comprises 144 modules arranged as an array having 72 rows and two columns. However, it should be appreciated that a substrate of an ultrasound device 100 may comprise any suitable number of ultrasound circuitry modules (e.g., at least two modules, at least ten modules, at least 100 modules, at least 1000 modules, at least 5000 modules, at least 10,000 modules, at least 25,000 modules, at least 50,000 modules, at least 100,000 modules, at least 250,000 modules, at least 500,000 modules, between two and a million modules, etc.) that may be arranged as an two-dimensional array of modules having any suitable number of rows and columns or the ultrasound circuitry modules may be arranged in any other suitable way.

In the illustrated embodiment, each module 204 comprises 64 ultrasound elements arranged as an array having two rows and 32 columns. However, it should be appreciated that an ultrasound circuitry module 204 may comprise any suitable number of ultrasound elements (e.g., one ultrasound element, at least two ultrasound elements, at least four ultrasound elements, at least eight ultrasound elements, at least 16 ultrasound elements, at least 32 ultrasound elements, at least 64 ultrasound elements, at least 128 ultrasound elements, at least 256 ultrasound elements, at least 512 ultrasound elements, between two and 1024 elements, etc.) that may be arranged as a two-dimensional array of ultrasound elements having any suitable number of rows and columns or in any other suitable way, In the illustrated embodiment, each ultrasound element 206 comprises 16 ultrasonic transducers arranged as a two-dimensional array having four rows and four columns. However, it should be appreciated that an ultrasound element 206 may comprise any suitable number of ultrasonic transducers (e.g., one, at least two, at least four, at least 16, at least 25, at least 36, at least 49, at least 64, at least 81, at least 100, between one and 200, etc.) that may be arranged as a two dimensional array having any suitable number of rows and columns (square or rectangular) or in any other suitable way. Alternatively, the ultrasonic transducers may be arranged in any other suitable geometric array including, but not limited to, a hexagonal array, a triangular array, and a skewed lattice.

Each ultrasound circuitry module 204 may comprise or be associated with circuitry in addition to one or more ultrasound elements. For example, an ultrasound circuitry module may comprise circuitry associated with transmitting acoustic waves including, but not limited to, one or more waveform generators (e.g., two waveform generators, four waveform generators, etc.), encoding circuitry, and decoding circuitry. In some embodiments, all or a portion of an ultrasound circuitry module may additionally or alternatively comprise or be associated with any other suitable circuitry. For example, in some embodiments, each module 204 may be associated with receive-side components including, but not limited to, analog signal chain elements and digital signal processing elements, as described briefly above, and described in more detail below.

In some embodiments, each module may include eight receive channels, and each of the eight receive channels may be associated with a single timing and control circuit or other control elements including, but not limited to, a time gain compensation circuit, as discussed in more detail below. Additionally, each module may be associated with multiple components to perform analog and/or digital signal processing to output signals from the receive channels of the module. For example, such components may include, but are not limited to, components of the analog receive chain and components of the digital signal processing circuitry such as memory, multiplier circuits, and adder circuits.

In some embodiments, the ultrasound device may comprise module interconnection circuitry integrated with the substrate and configured to connect ultrasound circuitry modules to one another to allow data to flow among the ultrasound circuitry modules. For example, the device module interconnection circuitry may provide for connectivity among adjacent ultrasound circuitry modules. In this way, an ultrasound circuitry module may be configured to provide data to and/or receive data from one or more other ultrasound circuitry modules on the device.

It should be appreciated that communication between one or more of the illustrated components may be performed in any of numerous ways. In some embodiments, for example, one or more high-speed busses (not shown), such as that employed by a unified Northbridge, may be used to allow high-speed intra-chip communication or communication with one or more off-chip components. In some embodiments, one or more modules may be connected using an interconnection network. For example, a shift register ring communication network may be used where neighboring modules communicate with one another via the network.

In some embodiments, timing & control circuit 108 may, for example, be responsible for generating all timing and control signals that are used to synchronize and coordinate the operation of the other elements in the device 100. In the example shown, the timing & control circuit 108 is driven by a single clock signal CLK supplied to an input port 116. The clock signal CLK may, for example, be a high-frequency clock used to drive one or more of the on-chip circuit components. In some embodiments, the clock signal CLK may, for example, be a 1.5625 GHz or 2.5 GHz clock used to drive a high-speed serial output device (not shown in FIG. 1B) in the signal conditioning/processing circuit 110, or a 20 MHz, 40 MHz, or 200 MHz (or any other suitable speed) clock used to drive other digital components on the die 112, and the timing & control circuit 108 may divide or multiply the clock CLK, as necessary, to drive other components on the die 112. In other embodiments, two or more clocks of different frequencies (such as those referenced above) may be separately supplied to the timing & control circuit 108 from an off-chip source.

In the example shown, one or more output ports 114 may output a data stream generated by one or more components of the signal conditioning/processing circuit 110. Such data streams may, for example, be generated by one or more USB 2.0 modules, one or more USB 3.0 modules, one or more USB 3.1 modules, one or more Thunderbolt modules, one or more FireWire modules, and/or one or more Gigibit (e.g., 10 GB, 40 GB, or 100 GB) Ethernet modules, integrated on the die 112. In some embodiments, the signal stream produced on output port 114 can be provided as input to an electronics device including, but not limited to, a cloud service, one or more computers, a tablet, and/or a smartphone. The one or more electronic devices receiving the signal stream may generate and/or display numerical values, 1-dimensional, 2-dimensional, 3-dimensional, and/or tomographic images. In some embodiments, the signal stream output on output port 114 may be provided to one or more additional off-chip circuits for additional processing, as discussed below in connection with FIG. 3.

In embodiments in which image reconstruction capabilities are incorporated in the signal conditioning/processing circuit 110 (as explained further below), even relatively low-power devices, such as smartphones or tablets which have only a limited amount of processing power and memory available for application execution, can display images using only a data stream from the output port 114. Examples of high-speed serial data modules and other components that may be included in the signal conditioning/processing circuit 110 are discussed in more detail below. Performing at least a portion of an image reconstruction process on-chip and transmitting the output of the at least a portion of the image reconstruction process off-chip using a data link is one of the features that may facilitate an integrated "ultrasound on a chip" solution that can be used with a wide range of external display devices having varying degrees of processing power in accordance to some embodiments of the present disclosure.

In various embodiments, each RX control circuit 106 may be associated with a single transducer, a group of two or more transducers within a single transducer element, a single transducer element comprising a group of transducers, a group of two or more transducer elements within a module, a single module comprising two or more transducer elements, two or more modules in an array 102, or an entire array 102 of transducers.

In the example shown in FIG. 1B, there is a separate RX control circuit 106 for each transducer in the array(s) 102, but there is only one instance of each of the timing & control circuit 108 and the signal conditioning/processing circuit 110. Accordingly, in such an implementation, the timing & control circuit 108 may be responsible for synchronizing and coordinating the operation of all RX control circuit 106 combinations on the die 112, and the signal conditioning/processing circuit 110 may be responsible for handling inputs from all of the RX control circuits 106 on the die 112. Alternatively, die 112 may include multiple timing & control circuits 108, with each of the timing & control circuits being responsible for synchronizing and coordinating the operation of a subset of RX control circuit combinations on the die.

As discussed above, in some embodiments, at least some of the receive-path digital signal processing electronics discussed above in connection with FIG. 1B, may be implemented off-chip to reduce the size of the ultrasound-on-a-chip architecture, to reduce power consumption of the ultrasound device 100, or for any other reason including, but not limited to, providing advanced image reconstruction capabilities using one or more off-chip processors.

Figure 3:
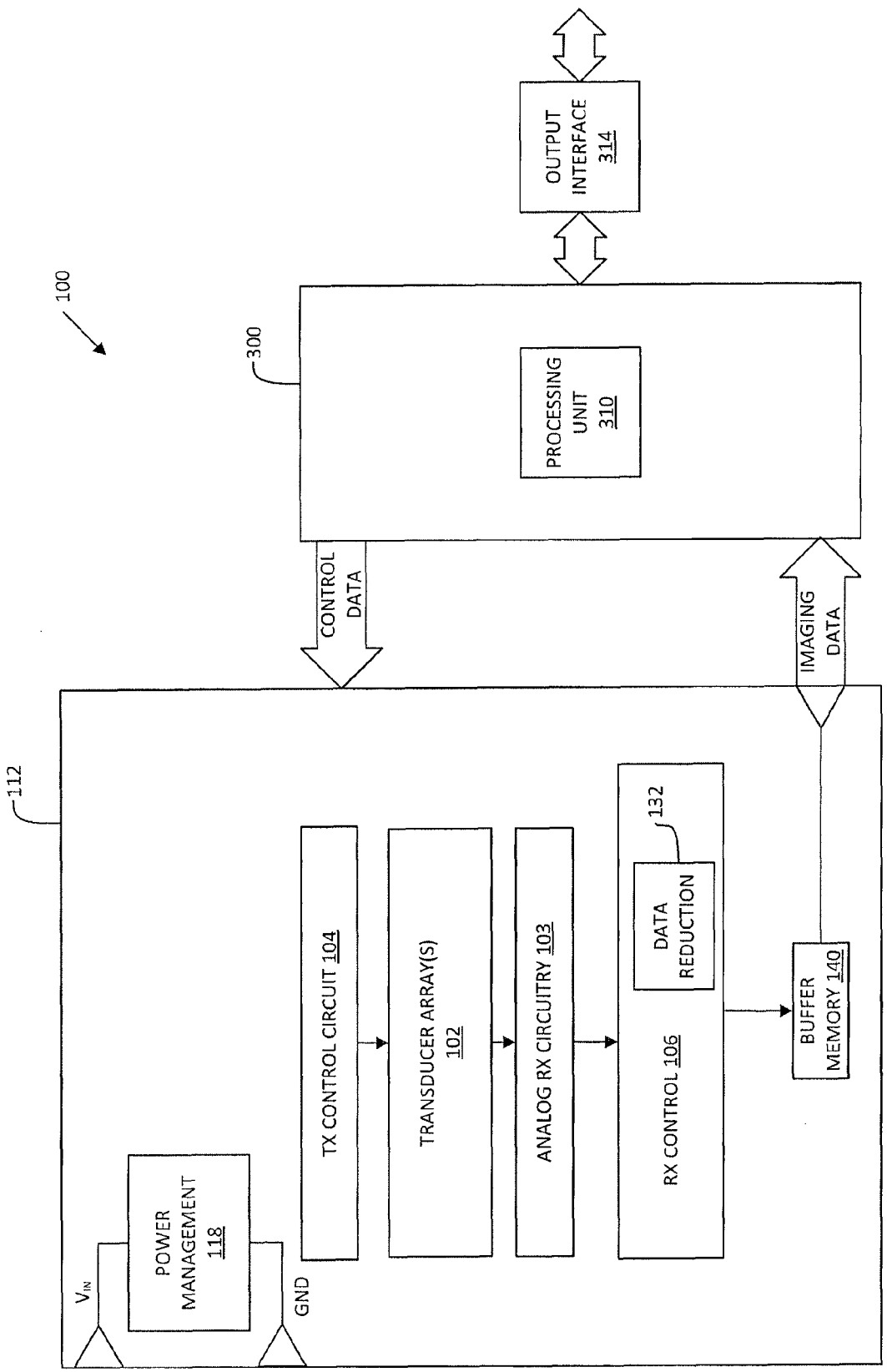
FIG. 3 shows an alternative illustrative architecture in which at least some digital processing components are located off-chip, in accordance with some embodiments of the present disclosure.

FIG. 3 shows an illustrative embodiment of ultrasound device 100 in which a portion of the receive-path digital signal processing circuitry is implemented off-chip. In the illustrated embodiment, field-programmable gate array (FPGA) 300 is connected to portions of device 100 implemented on substrate 112. FPGA 300 is configured to perform at least some signal processing operations described above as having been performed in the embodiment shown in FIG. 1B. For example, FPGA 300 may include processing unit 310 configured to receive imaging data from buffer memory 140 and perform image reconstruction or any other suitable operation on the received imaging data. Additionally, FPGA 300 may be configured to transmit control data to the portion of ultrasound device 100 integrated on substrate 112. The control data may include control parameters to control operation of transmit control circuitry 104 and/or receive-side circuitry including, but not limited to, analog TX circuitry 104, analog RX circuitry 103, and RX control circuit 106. FPGA 300 may be further configured to send processed imaging data to output interface 314 for transmission to any suitable device for display and/or further processing, as discussed above. Any suitable data interface may be used to transfer data between die 112 and FPGA 300 using output port 114, and embodiments of the present disclosure are not limited in this respect. In some embodiments, a digital signal processor (DSP), an embedded controller, or any other digital circuit logic may be used in addition to, or as an alternative to, FPGA 300 for providing at least a portion of the receive-path digital circuitry off-chip.

As discussed above, in some embodiments, RX control circuitry 106 may include a time gain compensation (TGC) circuit 160 configured to provide digital control of an analog variable gain amplifier (VGA) to process signal outputs from the ultrasound transducer elements. TGC circuit 160 compensates for signals received from different depths in an imaged object (e.g., by controlling the VGA to provide variable gain for signals received at different times).

Figure 4:
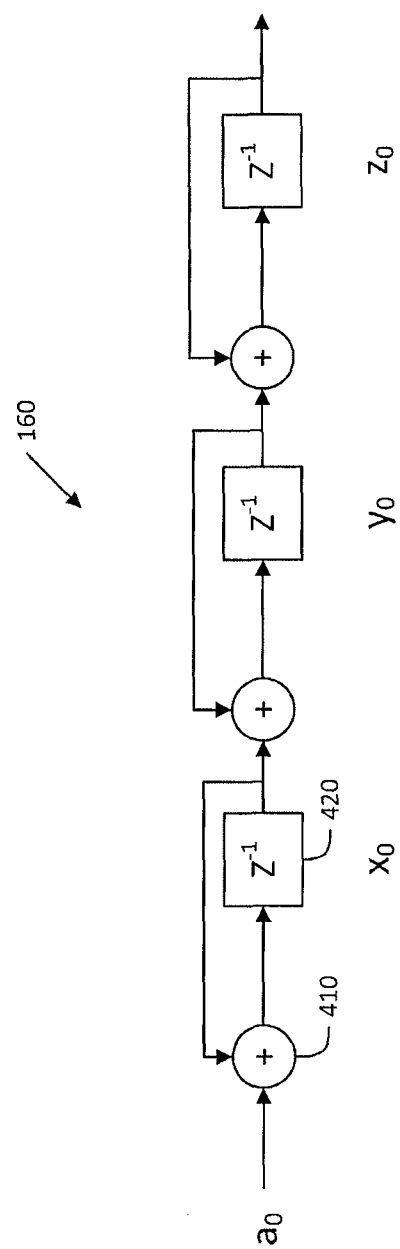
FIG. 4 shows an illustrative architecture for a time gain compensation circuit that may be used in accordance with some embodiments of the present disclosure.

In one embodiment, output from the VGA is stored in a memory, and VGA values are read from the memory at the TGC circuit update rate. FIG. 4 illustrates an example architecture of a TGC circuit 160 that may be used in accordance with some embodiments of the present disclosure, and requires less memory and fewer programming words than the aforementioned embodiment that reads VGA values from memory at the update rate of the TCG circuit. The illustrated TGC circuit 160 is implemented as a multi-stage summing control circuit that controls an analog variable gain amplifier, which amplifies signals received from greater depths compared to signals received from shallower depths. TGC circuit 160 includes controlling circuitry elements including adder 410 and delay element 420.

In some embodiments, TGC circuit 160 may be configured to model a corrective gain profile for the variable gain amplifier with a piecewise polynomial (i.e., composed of multiple polynomial segments). The gain profile may be designed (manually by a user and/or automatically) to match the signals output from the ultrasound transducer elements. The piecewise polynomial model may be of any order including, but not limited to, a third order polynomial model. One implementation for modeling a piecewise polynomial is to use three stages of an integrator circuit, as shown in FIG. 4. Other order polynomials can similarly be implemented by using more or less stages. In some embodiments, the piecewise polynomial is modeled using a variable input update rate, which is the rate at which a control signal for controlling a variable gain amplifier circuit is updated. Illustrative input update rates for updating the control signal include update rates ranging between 100 kHz and 1.25 MHz, or may include other suitable values including update rates ranging from below 100 kHz to the update rate of an ADC on the chip (e.g., 50 MHz). In some embodiments, the spacing between updates of the control signal is non-uniform resulting in a variable input update rate. Other update rates including the calculation update rate and the output update rate may be based on internal registers and may be constant (e.g., 50 MHz, 100 MHz, or 200 MHz) or variable. In particular, the calculation update rate for updating the polynomial coefficients may be fixed or variable. It should be appreciated that any suitable input, calculation, and output update rates may alternatively be used.

In some embodiments, the parameterization of the variable gain profile provided by the TGC circuit 160 may be programmable, such that the piecewise polynomial function may be calculated dynamically, and may be programmed differently based on a selected imaging mode and/or imaging application. For example, in order to program multiple segments of a piecewise polynomial function, the parameters (e.g., x0, y0, z0, and duration) may be changed dynamically during a TGC curve evaluation to implement subsequent polynomial segments. In some embodiments, all parameters (including the duration parameter) may be programmed for each piecewise segment of the polynomial function. Alternatively, a subset (i.e., fewer than all) of the parameters may be changed dynamically for each segment. For example, in one implementation, only the a0 parameter is changed between polynomial segments. In some embodiments, each module (e.g., comprising eight receive channels) may be associated with a single TGC circuit 160. Alternatively, multiple TGC circuits may be associated with each module, and embodiments are not limited in this respect.

Illustrative Types of Compression

Ultrasound imaging devices provided in accordance with some embodiments of the present disclosure record a large amount of ultrasound data to provide quality images using an array of ultrasonic transducer elements, as discussed above. To process this large amount of data and transfer the data off-chip at an acceptable rate using an output data interface module having a maximum data bandwidth, some embodiments employ on-chip circuitry to compress the data from the ultrasonic transducer elements prior to transmitting the data off-chip. The inclusion of on-chip data compression elements may thus further facilitate and/or enhance an "ultrasound-on-a-chip" solution in accordance with some embodiments.

In some embodiments, different types of compression may be selected depending on the imaging goals and/or mode of operation of the ultrasound imaging application. For example, the different types or amounts of compression used may depend, at least in part, on an acceptable image quality for a particular imaging application. Examples of on-chip compression that may be implemented in accordance with embodiments of the present disclosure include, but are not limited to, spectral compression, aperture compression, excitation compression, ensemble compression, entropy compression, signal value compression, and selective omission compression, each of which is described in more detail below.

Spectral compression compresses data by operating on the frequency content of a received acoustic signal. Spectral compression downsizes an amount of spectral bandwidth to only that which is necessary to achieve a desired image resolution. Examples of spectral compression include, but are not limited to, quadrature demodulation and filtered downsampling, each of which is described in more detail below.

Aperture compression limits the cross-range bandwidth of the acoustic signal to only that which is needed to achieve a desired lateral image resolution. Examples of aperture compression include, but are not limited to, filtered downsampling and other filtering techniques described in more detail below.

Excitation compression compresses data by combining excitations in a unique way in which redundant information between excitations are compressed together. A non-limiting example of excitation compression is to form an image from the excitations, where all excitations have been compressed into one image reconstruction.

Ensemble compression reduces data redundancy in ensemble imaging by calculating relevant information. A non-limiting example of ensemble compression is Doppler processing, described in more detail below, where multiple images are compressed into a single complex velocity and power reconstruction profile.

Entropy compression reduces information redundant in data communication as it is provided off-chip. Encoding frame-to-frame differences rather than encoding the full data for each frame is a non-limiting example of entropy compression.

Signal value compression reduces data to values corresponding to a desired interest in characteristics (e.g., power, max value, variance) of the overall signal. Non-limiting examples of signal value compression include compression circuitry that calculates the total power in a signal and compression circuitry that determines a time-of-flight for received acoustic signals for characterization processes.

Selective omission compression reduces an amount of data by selectively omitting data from the full set of data. Non-limiting examples of selective omission compression include re-quantization, described in more detail below, and sparse aperture imaging.

On-chip circuitry, discussed in more detail below, for performing compression of acoustic data signals received from an array of ultrasonic elements may be implemented to perform one or more of the types of compression discussed above. In some embodiments, a data signal may be compressed to be transmitted off-chip in accordance with one or more operating parameter requirements. For example, in some embodiments, the compressed data signal is compressed such that it may be transmitted out of the semiconductor die as a data stream at a rate of less than or equal to four Gigabits per second or at some other suitable rate. In some embodiments, the data signal may be compressed by a factor of greater than one but less than two. In some embodiments, the data signal may be compressed by at least a factor of two and less than a factor of four. In some embodiments, the data signal may be compressed by at least a factor of four and less than a factor of ten. In some embodiments, the data signal may be compressed by at least a factor of ten and less than a factor of twenty. In some embodiments, the data signal may be compressed by at least a factor of twenty and less than a factor of one hundred. In other embodiments, the data signal may be compressed by at least a factor of one hundred and less than a factor of one thousand. In some embodiments, the data signal may be compressed by at least a factor of one thousand and less than a factor of ten thousand. It should be appreciated that any suitable amount of compression may alternatively be used, and the ranges discussed above for compression amount are provided merely for illustrative purposes.

In some embodiments, the ultrasound imager may be configurable to operate in a plurality of imaging modes (e.g., 2D, 3D), and the type and/or amount of compression (including no compression) used may depend, at least in part, on the particular operating mode of the ultrasound imager. For example, different operating modes may be programmed to generate different amounts of data, and the type and/or amount of compression used may be based, at least in part, an amount of data generated when a particular operating mode is selected, such that the data may be provided off-chip at a desired rate compatible with output interface 314. Although the amount of generated data may be one factor that determines a type and/or amount of compression used for different operating modes, it should be appreciated that other factors may additionally or alternatively be considered when determining a type and/or amount of compression to use for a selected operating mode. For example, image quality requirements for a particular imaging application may be considered.

The selection of an operating mode for the ultrasound imager may be made in any suitable way. For example, in some embodiments the ultrasound imager may operate in one of a plurality of imaging modes in dependence on a mode select signal (MODE) received from off-chip via input interface 200. Alternatively, the ultrasound imager may include on-chip memory configured to store an imaging mode of operation and an amount and/or type of compression (including no compression) may be determined based, at least in part, on the imaging mode of operation stored in on-chip memory.

Additionally, compression may be applied to data at different stages in the signal processing chain. As discussed in further detail below, data compression in the receive signal processing chain may be performed prior to image reconstruction, during image reconstruction, and/or after image reconstruction. In embodiments where image reconstruction is performed in part or entirely off-chip, on-chip architectures for data compression may be limited to one or more of the pre-image formation compression techniques discussed in more detail below. Example techniques and representative architectures for providing compression at each of these stages are provided herein.

Illustrative Pre-Image-Reconstruction Compression Architectures

On-chip data compression may be achieved prior to performing at least a portion of an image reconstruction process. For example, compression may be achieved by selectively acquiring and/or processing a number of measurements from the array of ultrasonic transducer elements that is less than the full set of measurements acquired/processed using the full array of elements. Compression using a reduced number of measurements may be implemented in any suitable way. In some embodiments, reducing a number of measurements comprises selecting an encoding scheme for an ultrasonic transducer element that reduces the number of measurements. For example, an encoding scheme associated with an encoding matrix such as a modified Hadamard matrix or a pseudorandom matrix may be used to reduce the number of measurements. In these types of encoding schemes, the signal sent to each element is multiplied by 1, 0, or −1 based on the position of the element and the frame number. The weights are selected such that the sequence of weightings for a given element is equal to a column of a Hadamard or pseudorandom matrix (each element will typically have a unique column).

Figure 5:
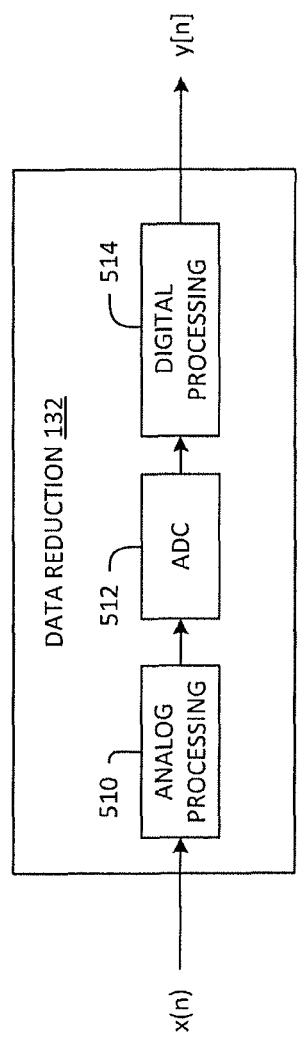
FIG. 5 shows an illustrative architecture for a data reduction circuit that may be incorporated in some embodiments of the present disclosure.

In some embodiments, pre-image reconstruction data compression may also be achieved by using on-chip compression circuitry components included as a portion of data reduction circuit 132, discussed above. FIG. 5 shows a block diagram of components that may be included within data reduction circuit 132 of each RX control circuit 106 (e.g., see FIG. 1B and FIG. 3). As shown in FIG. 5, data reduction circuit 132 may include an analog processing block 510 configured to perform analog data compression techniques. For example, analog processing block 510 may include a low-pass filter (LPF) that filters the input signal x(n). The LPF in analog processing block 510 may provide for anti-aliasing of the input signal. In some embodiments, the LPF may, for example, comprise a second-order low-pass filter having a frequency cutoff on the order of 5 MHz, on the order of 10 MHz, on the order of 25 MHz, or on the order of 50 MHz. Other implementations are, however, possible and contemplated. For example, analog processing block may additionally or alternatively include a high-pass filter, a band-pass filter or any other suitable analog components for processing input signal x(n). For example, some embodiments may include one or more of the following analog components: amplifiers, signal combiners, attenuators, mixers, and analog delay circuits. As discussed above, any data reduction functionality described herein implemented using analog components may alternatively be implemented using, at least partially, digital components, and vice versa, and embodiments are not limited based on whether particular data reduction functionality is implemented using analog components, digital components, or a combination of analog and digital components.

Data reduction circuit 132 as shown also includes analog-to-digital converter (ADC) 512 configured to convert the analog signal (or alternatively a filtered, or otherwise processed version of the analog signal) to a digital representation. For example, ADC 512 may, for example, comprise a 10-bit, 20 Msps, 40 Msps, 50 Msps, 80 Msps ADC, or any other suitable ADC. Illustrative types of ADCs that may be used include, but are not limited to, a successive approximation register (SAR) ADC, a flash ADC, a pipeline ADC, a sigma-delta ADC, a multi-slop ADC, and a time-interleaved ADC.

After the signal has been converted into a digital representation by ADC 512, the signal is transmitted to digital processing block 514 of data reduction circuit 132. The digital processing block 514 may, for example, be configured to reduce a data bandwidth of the digital representation of the acquired signal using one or more digital signal processing architectures. For example, the digital signal processing architectures may be configured to perform one or more data reduction techniques including, but not limited to, quadrature demodulation, downsampling, quadrature sampling, filtered downsampling, cascade integrating comb (CIC) filtering, receive aperture filtering, polyphase filtering, re-quantization, and pulse compression, as described in more detail below.

As discussed above, some embodiments include digital signal processing components that provide one or more stages of data compression to enable a large amount of data received by ultrasonic transducer elements to be transmitted off chip at a rate compatible with the limited bandwidth of an output interface module. Such compression facilitates an ultrasound-on-a-chip solution in accordance with some embodiments. In some embodiments, one or more of the stage(s) of data compression may be enabled or disabled depending on a particular mode of operation of the ultrasound device, as discussed above.

Figure 6:
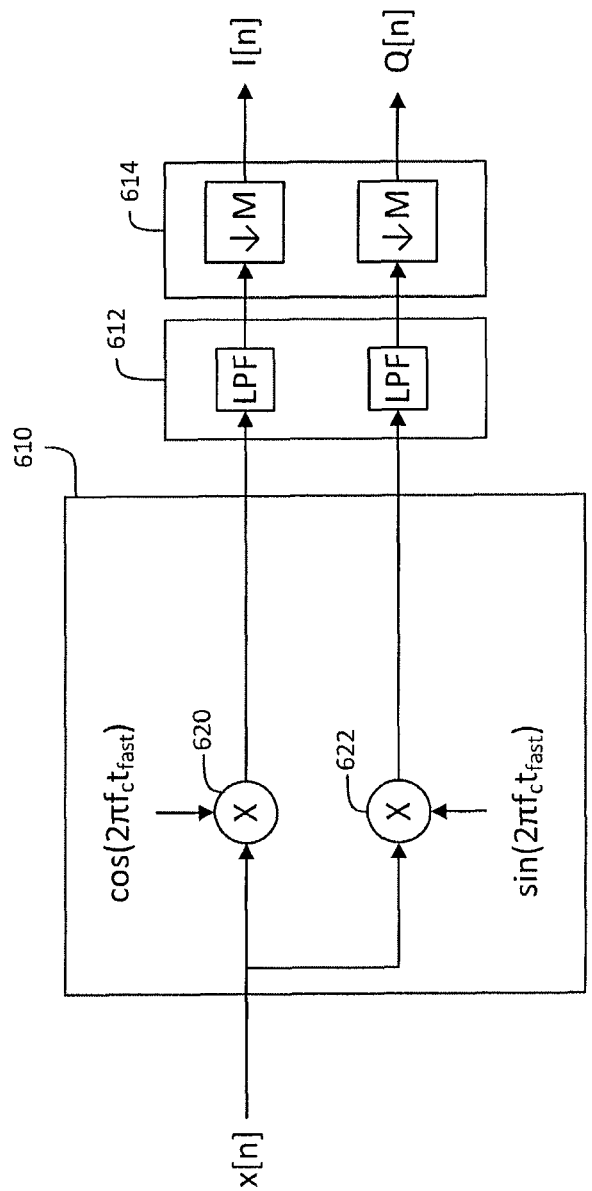
FIG. 6 shows an illustrative architecture for data reduction within a digital processing block of the data reduction circuit shown in FIG. 5.

FIG. 6 shows an illustrative architecture for at least a portion of digital processing block 514 of the data reduction circuit 312 shown in FIG. 5. In the illustrated embodiment, the digital processing block 514 performs quadrature demodulation (QDM), which is a form of spectral compression. QDM reduces the amount of bandwidth that must be processed and stored by an ultrasound imaging system in accordance with embodiments of the present disclosure. In particular, QDM mixes down the digitized version of the received signal x[n] from center frequency to baseband. The baseband signal may then be low-pass filtered and decimated, as discussed in more detail below. The illustrated QDM circuit may allow for a lossless (or nearly lossless) reduction of bandwidth by removing unused frequencies from the received signal, thus significantly reducing the amount of digital data that needs to be subsequently processed and offloaded from the chip. The bandwidth reduction achieved by these components may help to facilitate and/or improve the performance of the "ultrasound-on-a-chip" embodiments described herein.

FIG. 6 shows that a QDM circuit may be implemented as two separate data streams for the imaginary (I[n]) and quadrature (Q[n]) portions of the complex input signal x[n]. Heterodyne circuit 610 includes a numerically-controlled oscillator, or any other suitable component, that may be used to generate $\cos(2\pi f_c t)$ and $\sin(2\pi f_c t)$, where the center frequency $f_c$ is selected to provide a particular amount of demodulation. Demodulation may phase modulate a signal to be centered at 0 Hz or bounded by some desired frequency range for filtering. In some embodiments, it may be desirable to match $f_c$ with a frequency of interest of the transducer cells that are used in the array(s) 102. The imaginary and quadrature data streams from heterodyne circuit 610 are further processed by filtering circuit 612 and decimation circuit 614 prior to output. Filtering circuit 612 is illustrated as performing low-pass filtering (LPF). However, it should be appreciated that other types of filtering, such as band-pass filtering (BPF) and high-pass filtering (HPF) may alternatively be used in filtering circuit 612. Example circuit architectures for providing quadrature demodulation are described in more detail below.

Figure 7:
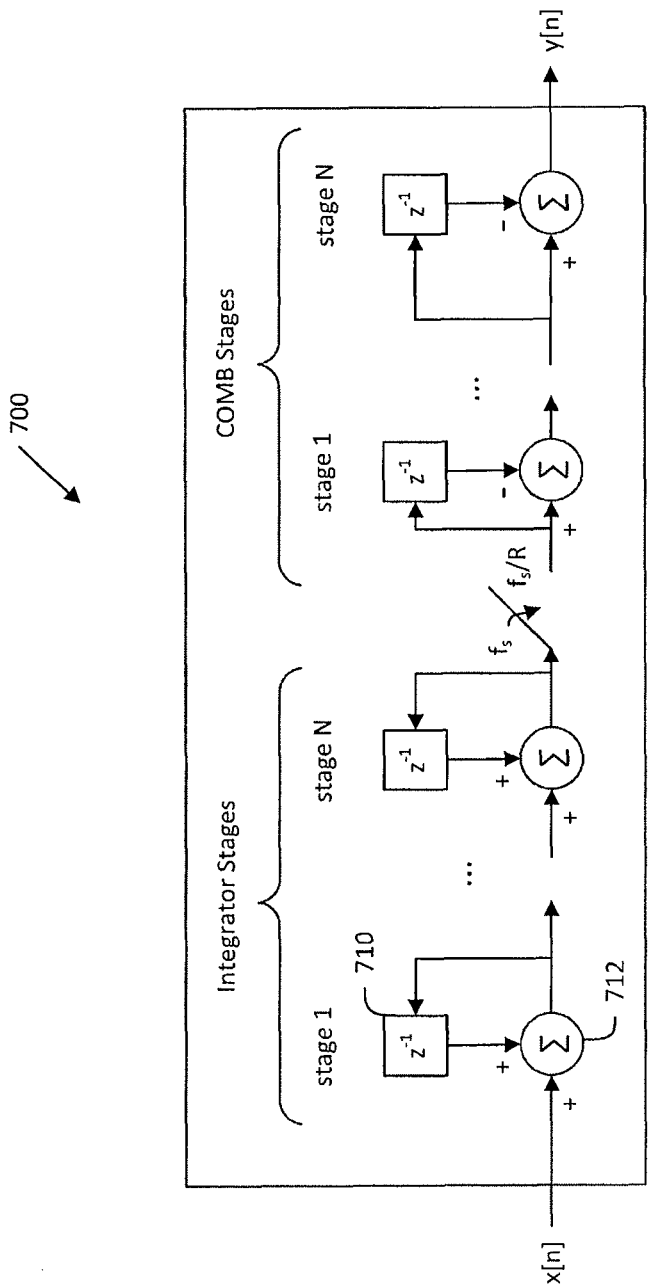
FIG. 7 shows an illustrative architecture for a cascade integrating comb circuit that may be used in accordance with some embodiments of the present disclosure.

In some embodiments of the present disclosure, a cascade integrating comb (CIC) filter architecture may be used to perform filtering (e.g., for filtering circuit 612) and decimation (e.g., for decimation circuit 614). For example, such a CIC filter architecture may be used to accurately calculate a range value using a precise delay time index. An illustrative CIC filter is shown in FIG. 7. As shown, CIC filter 700 includes delay elements 710 and integrator elements 712. The CIC filter includes a plurality (N) stages and acts as a low-pass filter, while decimating the input data stream x[n] to produce an output data stream y[n]. Increasing the number of stages results in more droop in the passband, while increasing the number of stages results in better image rejection. In some implementations, passband droop may be at least partially addressed using a compensation filter that is applied after the CIC filter has been applied to the data.

Figure 8:
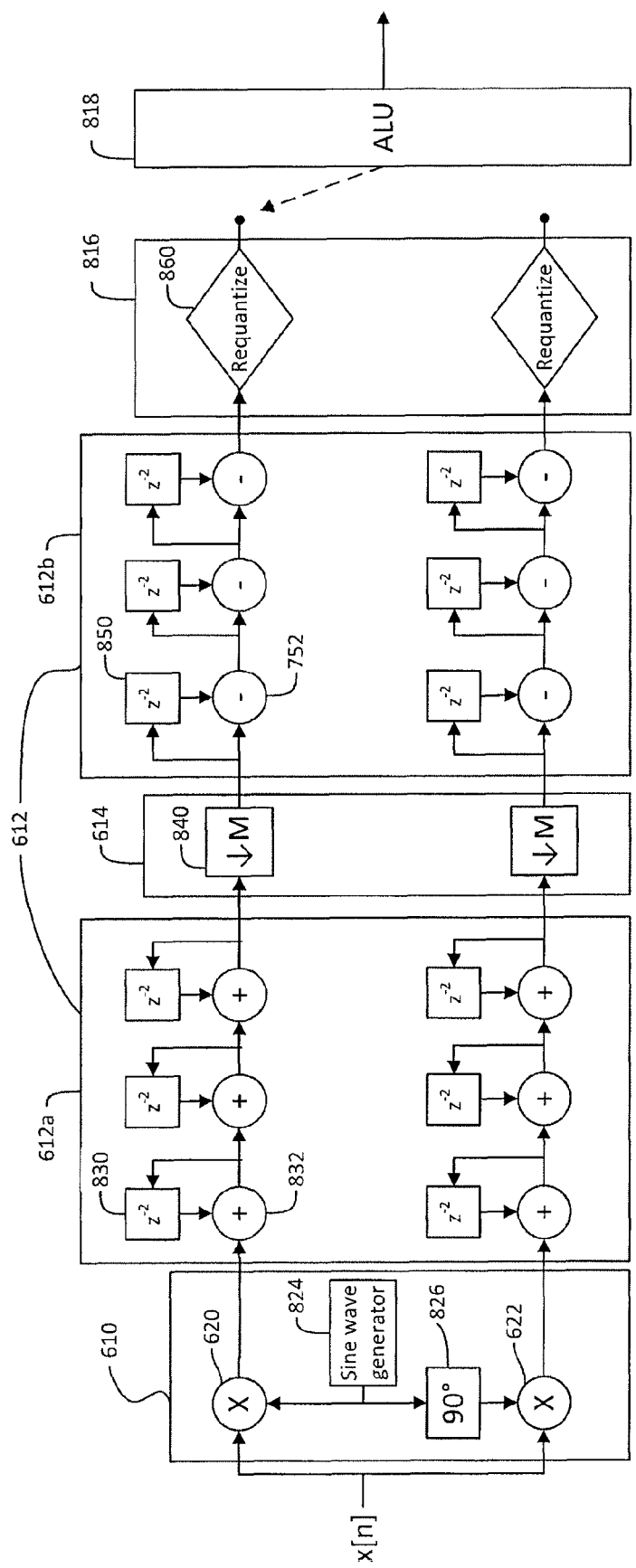
FIG. 8 shows an illustrative circuit for performing data reduction in accordance with some embodiments of the present disclosure.

FIG. 8 shows an illustrative circuit for performing digital signal processing, including quadrature demodulation, in accordance with some embodiments of the present disclosure. As illustrated, the circuit of FIG. 8 includes six stages of processing implemented in digital processing circuitry. It should be appreciated that any number of digital processing stages may be included, and the six-stage implementation shown in FIG. 8 is provided merely for illustration. Additionally, some modes of operation of the ultrasound imaging device may employ some, but not all of the digital signal processing functionality described in FIG. 8 to provide different amounts and/or types of compression (including no compression) for particular applications. Mode selection and subsequent activation/deactivation of digital signal processing components may be achieved using any suitable technique, including, but not limited to, the techniques described above for mode selection.

As shown in FIG. 8, received digital signal x[n] is first processed by heterodyne circuit 610, which includes a pair of multiplier circuits 620, 622, a sine wave generator 824, and a phase shifter element 826. The outputs of heterodyne circuit 610 are passed to a low pass filter (LPF) 612. In the illustrative architecture of FIG. 8, LPF 612 is shown as a portion of a cascade integrating comb (CIC) filter that includes an integrator stage 612a and a comb stage 612b. It should be appreciated that any suitable low-pass filter may be used for LPF 612, but preferably, LPF 612 should be sufficient to reject high-frequency images from the multiply operation of heterodyne circuit 610 and anti-alias the signal before the downsampling provided by decimation circuit 614, described in more detail below.

In the illustrative architecture of FIG. 8, the outputs of heterodyne circuit 610 are provided to the integrator stage 612a of the CIC filter. As shown, integrator stage 612a includes delay elements 830 and adder elements 832. The outputs of the integrator stage 612a are passed to decimation circuit 614, which downsamples the received digital signal by a factor M using downsampling circuits 840. Any suitable amount of downsampling (M) may be used including, but not limited to, downsampling by M=2, 4, 6, 8, and 16. A downconversion of M=4 produces half the amount of data that was input (one-fourth the sample rate, but twice the number of data channels).

The outputs of decimation circuit 614 are passed to the comb stage 612b of the CIC filter. As shown, comb stage 612b includes delay elements 850 and subtraction elements 852. The outputs of the comb stage 612b are passed to re-quantization circuit 816, where re-quantization of the digital signals is performed using re-quantization circuits 860, as discussed in more detail below. The outputs of re-quantization circuit 816 are passed to arithmetic logic unit (ALU) 818, which provides additional arithmetic processing, examples of which are discussed in more detail below with regard to FIG. 14. In some embodiments, the ALU 818 may be an optimized integrated ALU.

The output of digital processing block 514 may be provided to additional processing stages (e.g., image reconstruction processing) formed on the same or different substrate as digital processing block 514. Additionally or alternatively, the output of digital processing block 514 may be stored in a buffer memory and may be provided via an output interface to additional off-chip processing components for further processing.

As discussed above, in some embodiments, digital processing block 514 may include circuitry for performing any suitable number of digital signal processing operations that provide compression of input data signal x[n], and embodiments of the present disclosure are not limited in this respect. For example, in one embodiment, digital processing block 514 may include a quadrature demodulation stage, a filtering stage, and decimation stage, and one or more of these stages may be configured to provide different levels of data compression based on the requirements of a particular imaging application.

Figure 9:
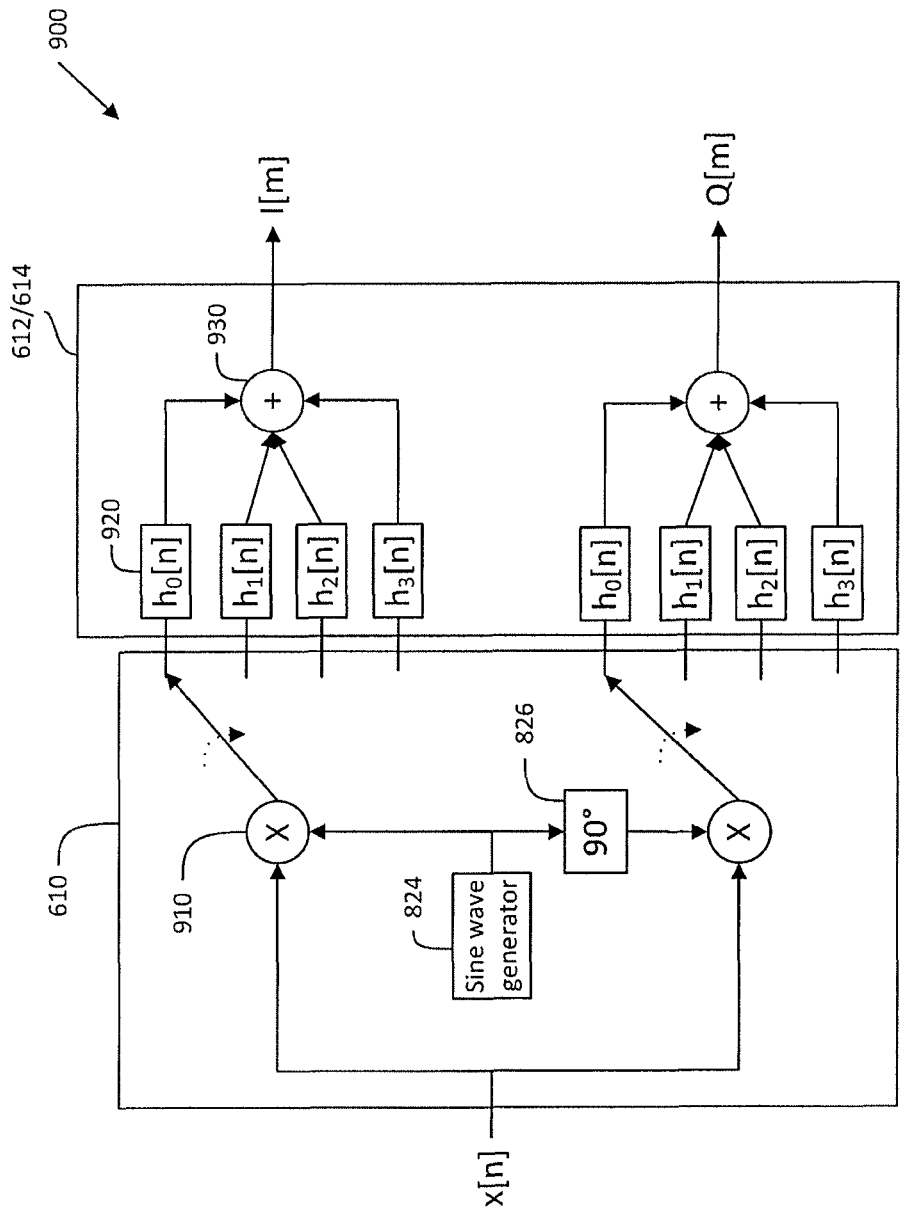
FIG. 9 shows an illustrative circuit for performing quadrature downsampling by a factor of four in accordance with some embodiments of the present disclosure.

FIG. 9 shows an illustrative polyphase architecture 900 of a QDM circuit using M=4 and a filter h[n]. The polyphase architecture 900 includes multiplier elements 910 and adder elements 930. The components 920 $h_0[n]$, $h_1[n]$, $h_2[n]$, and $h_3[n]$, which are determined based on the filter h[n], together implement a polyphase filter. The filter h[n] may have any desired bandwidth including, but not limited to, a quarter band filter, a half-band filter, a bandpass filter, or a highpass filter. Selection of a particular filtering architecture enables sampling different Nyquist zones during downconverting of the data.

Figure 10:
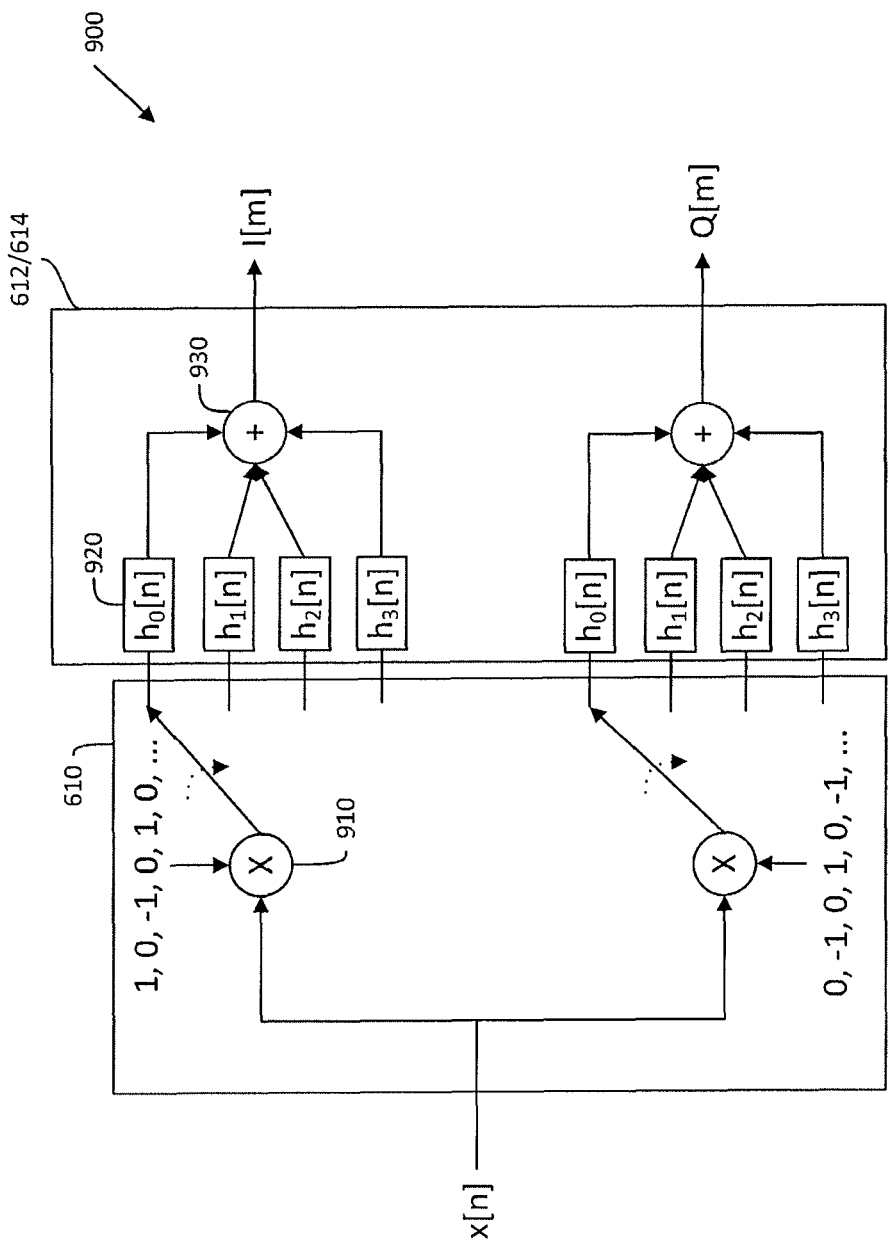
FIG. 10 shows an alternative circuit for performing quadrature downsampling by a factor of four in accordance with some embodiments of the present disclosure.

In the special case of quarter rate demodulation ($f_c = f_s/4$), the digital circuitry for the demodulation portion of the circuit of FIG. 9 may be simplified, as shown in FIG. 10. In place of the numerically-controlled oscillator (e.g., sine wave generator 824 and phase shifter element 826) is circuitry that samples every other element of the data stream, and then alternately inverts the samples. In some embodiments, the architecture of FIG. 10 (e.g., clocked at a rate of, $f_s*L/4$) may be further simplified using filter coefficients of h[n]=1, which allows for reduced hardware. Such an architecture may include a pair of accumulators that can sum or subtract samples into a running sum. It should be appreciated that the running sum may saturate (e.g., clip) or wrap based on a desired configuration.

Figure 11:
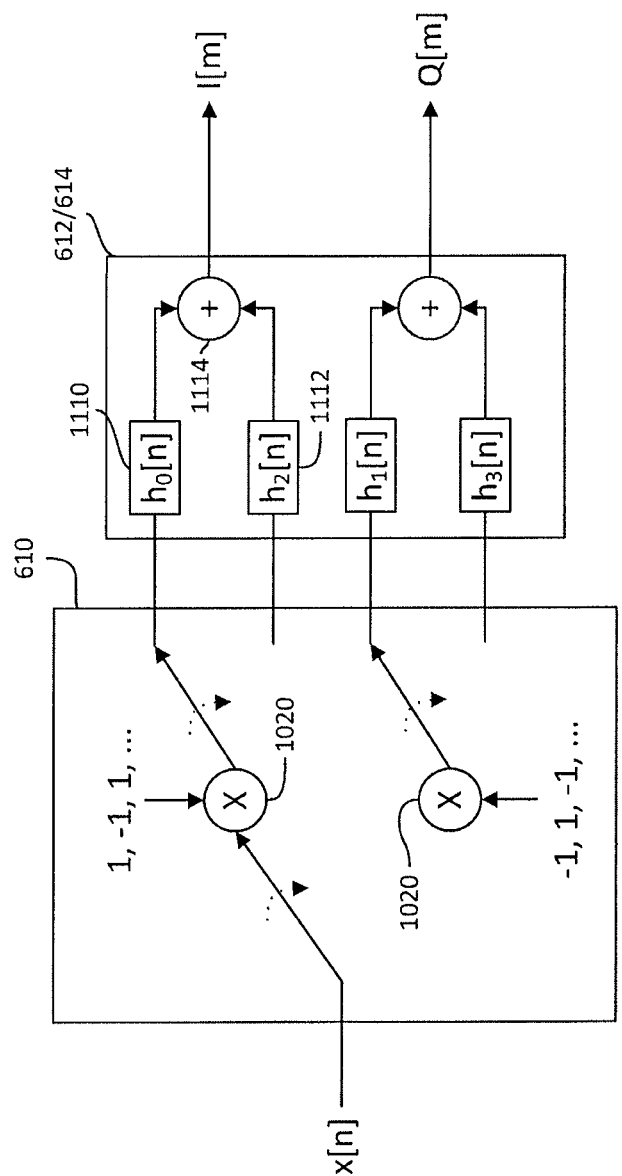
FIG. 11 shows an alternative circuit for performing quadrature downsampling by a factor of four in accordance with some embodiments of the present disclosure.
Figure 12:
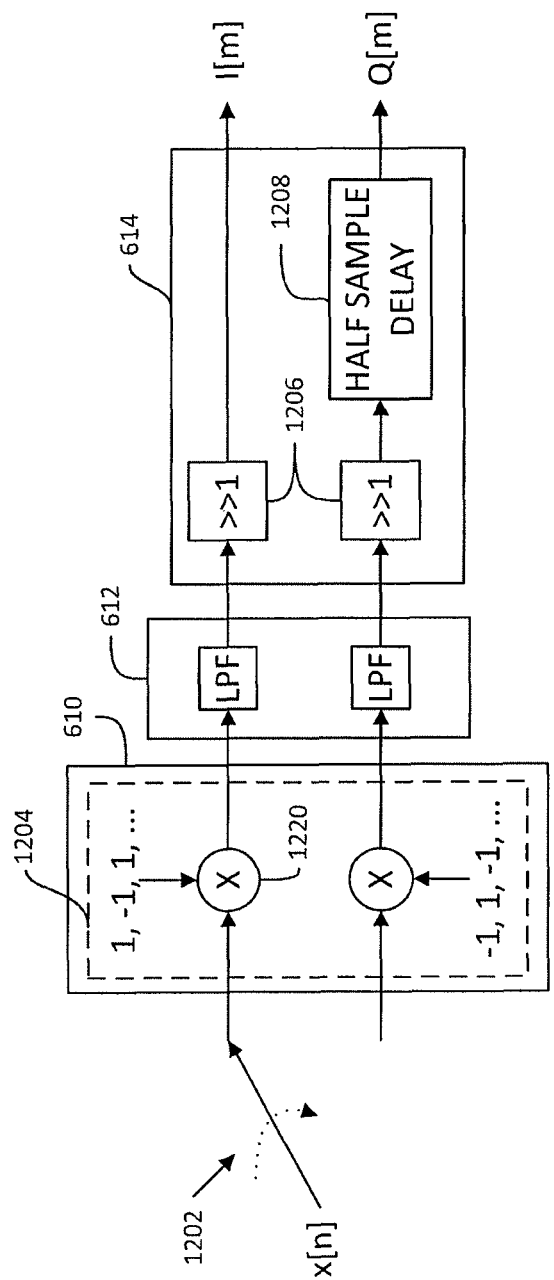
FIG. 12 shows an alternative circuit for performing quadrature downsampling by a factor of four in accordance with some embodiments of the present disclosure.

Due to the pattern of zero-value samples as input to the multipliers 910 in the architecture of FIG. 10, the circuitry to implement the polyphase half-band filter of FIG. 10 may further be simplified as shown in FIG. 11. As shown, by removing the zero-value samples as input to the multipliers, the filters $h_1[n]$ and $h_3[n]$ may be removed in processing the signal I[m] and the filters $h_0[n]$ and $h_2[n]$ may be removed in processing the signal Q[m]. As shown in FIG. 12, the in-phase (I) component may be implemented by downsampling the input signal x[n] by a factor of two, flipping every other sample, and right-shifting the data by one sample. The same structure as for the in-phase component may also be used for the quadrature (Q) component by introducing a half sample delay as shown in FIG. 12. More specifically, the filters $h_0[n]$ and $h_2[n]$ may be reused in place of the filters $h_1[n]$ and $h_3[n]$ by implementing the half-sample delay shown in FIG. 12. Alternatively, the filters $h_1[n]$ and $h_3[n]$ may be reused in place of the filters $h_0[n]$ and $h_2[n]$ if the half sample delay is implemented in processing the in-phase (I) component rather than the quadrature (Q) component. Accordingly, at least a portion of the digital processing block 514 may be implemented in a digital architecture that includes an even-odd sampler 1202, a pair of inverters 1204 including multiplier elements 1220, a pair of right shifts 1206, and a half sample delay 1208. Data reduction techniques for reducing the data bandwidth may be achieved using values for M>2, as discussed in more detail below. Examples of additional components that may, in some embodiments, be included in digital processing block 514, in addition to or in lieu of a QDM circuit are described in further detail below.

Any suitable architecture for filtering and downsampling digital representations of ultrasound signals may be used in accordance with aspects of the present disclosure. In connection with the illustrative QDM circuit architectures described above, some embodiments may provide data compression using a polyphase filtering architecture. An illustrative architecture for polyphase filtering and an implementation example with a half-band decimating filter are described below in connection with FIG. 13.

Figure 13:
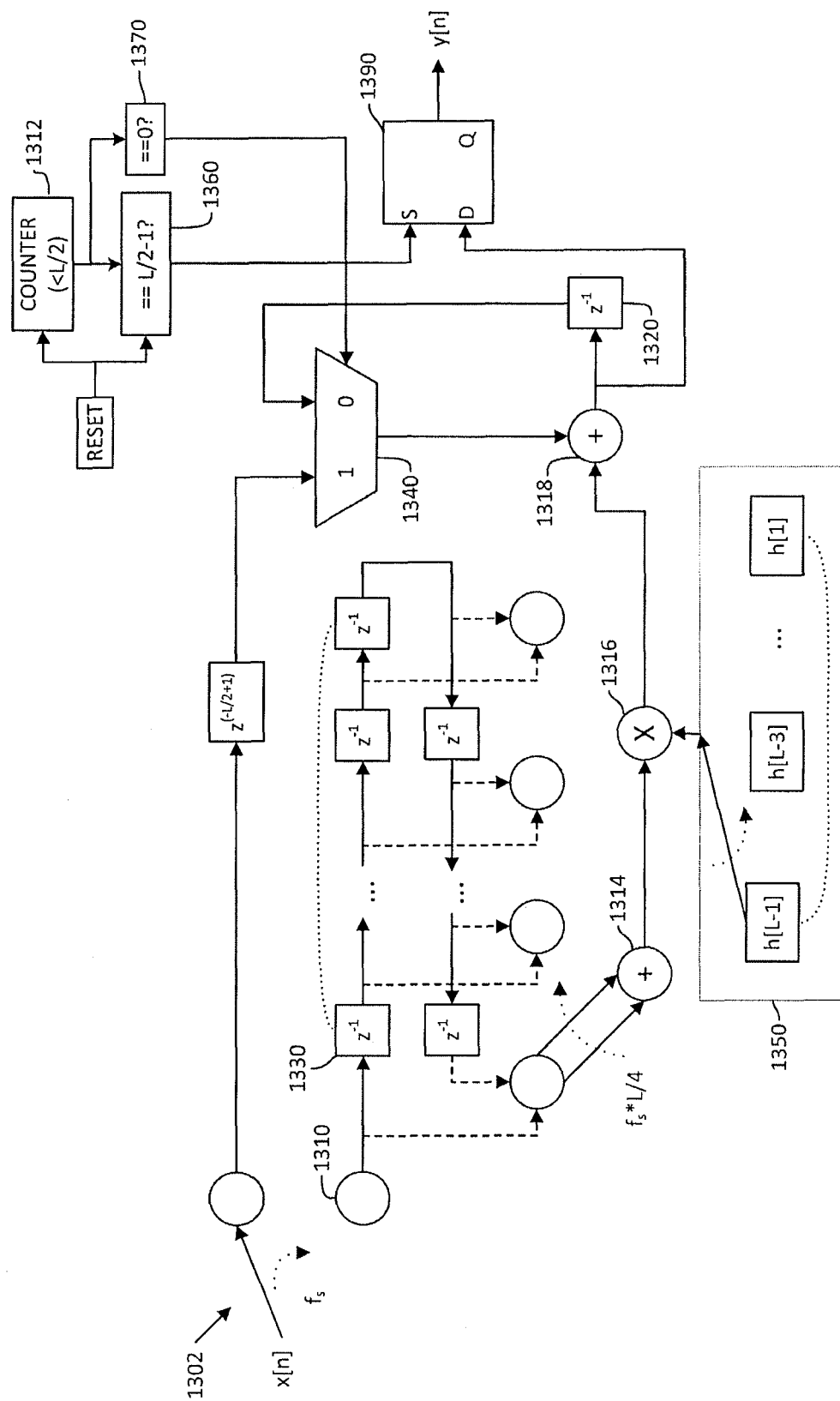
FIG. 13 shows an illustrative architecture for a polyphase filter that may be used in accordance with some embodiments of the present disclosure.

FIG. 13, described in more detail below, shows a half-band FIR filter architecture on the in-phase component of the generalized QDM circuit architecture of FIG. 9. In order to use the same filter structure for the quadrature component, the input to the Q component may be advanced by one sample following the multiplier, filtered and decimated, then corrected by applying a quarter-sample delay before adding I and Q. This architecture assumes a 2*L×1 point symmetric half-band filter (i.e., h[−(L−1)], . . . , h[L−1], such that h[2*n]=0 for all n≠0 and h[n]−h[−n] for all n).

As shown in FIG. 13, the input x[n] switches between two polyphase branches at a rate of $f_s$. When the switch 1302 is attached to the bottom branch, the node 1310 latches the value, the registers ($z^{-1}$) 1330 shift, and the counter 1312 begins. The computational blocks in the architecture are clocked at a rate of $f_s*L/4$ (e.g., the rate needed to complete L/2 multiplies within two input cycles—assuming one clock cycle to complete each multiply). The adder 1314 and the multiplier 1316 in the adder/multiplier pair perform the filtering step by combining symmetric sides of the filter, and then multiplying by the corresponding filter coefficient (e.g., h[1], . . . , h[L−1]) 1350. The adder/multiplier pair cycles through each tap of the filter to sum all of the polyphase components. The result of each multiplication is sent to an accumulator comprising adder 1318 and register 1320. Adder 1318 additionally receives values from logic element 1340. The accumulator may be initialized with a value equal to an appropriate center tap (e.g., which may be realized by the delay of L/2−1) when the counter is equal to zero as determined by block 1370. When the counter 1312 reaches L/2 as determined by block 1360, the result of the accumulator is latched to flip flop 1390, and the value of y[n] is output.

In addition to demodulation, filtering, and downsampling circuitry, other digital circuitry may also be incorporated as a portion of digital processing block 514 to provide additional or alternative modes of data compression that will facilitate and/or enhance an "ultrasound-on-a-chip" solution in accordance with some embodiments of the present disclosure. For example, some embodiments include re-quantization circuit 616 that performs re-quantization on the digital signal. Re-quantization may be implemented at any suitable position in the digital signal processing chain. For example, in some embodiments, re-quantization circuitry may be implemented immediately after analog-to-digital conversion. In other embodiments, re-quantization circuitry may be implemented as the last step prior to transmission of the data off-chip. In yet other embodiments, re-quantization circuitry may be implemented as an intermediate step of digital signal processing. Additionally, it should be appreciated that some embodiments may include multiple stages of re-quantization implemented at different locations in the digital signal processing chain.

Any suitable re-quantization technique may be used including, but not limited to, bit truncation, rounding, and clipping. In embodiments where bit truncation is used, the number of bits in a digital signal may be truncated based, at least in part, on a truncation level indicating the number of bits to be truncated. The truncation level may be configurable based on a selected imaging mode and/or using any other suitable criteria, such as a desired image quality. For example, the truncation level may be determined based, at least in part, on a maximum bandwidth of a data stream to be output and/or expected values for the digital signal to be truncated. In some embodiments, determining the expected values for the digital signal may be based, at least in part, on one or more of data from at least one previous acquisition, data from at least one previous frame, data from at least one previous sample in a same frame, and at least one time gain compensation curve value. For example, data from previous frames may be used to determine a truncation level for plane wave imaging, and using data from previous channels may be used to determine a truncation level for focused excitations. It should be appreciated that these applications of using previously received data to determine a truncation level are provided merely for illustration and are not limiting.

In embodiments where rounding is used, any suitable rounding technique may be employed including, but not limited to rounding half away from zero, rounding towards zero, always rounding up, always rounding down, rounding even up, rounding even down, rounding odd up, and rounding odd down.

In some embodiments, the re-quantizing circuit may, for example, determine a maximum magnitude of the incoming signal, scale all signals up to make the maximum signal full-scale, and then discard the lower N-bits from the signal. In other embodiments, the re-quantizing circuit may additionally or alternatively convert the signal to log space and keep only N bits of the signal. In yet other embodiments, the re-quantizing circuit may additionally or alternatively employ one or more of Huffman coding, arithmetic encoding, or vector quantization techniques. In yet other embodiments, noise shaping may be used. Noise-shaping circuitry feeds the error(s) between the actual and re-quantized value back into the input (either directly or indirectly, e.g., via a filter).

In some embodiments in which the ultrasound device is configured to employ coded-excitation pulses or linear frequency modulated (LFM) pulses, the receive-path signal processing electronics may include a stage that compresses the pulse as the emitted ultrasound waveform with a cross-correlation using a matched or mismatched filter. Pulse compression may be implemented using any suitable filter architecture including, but not limited to, using an finite impulse response (FIR) filter and using components to implement a Fast Fourier Transform (FFT), multiply, inverse Fast Fourier Transform (IFFT) algorithm.

Figure 14:
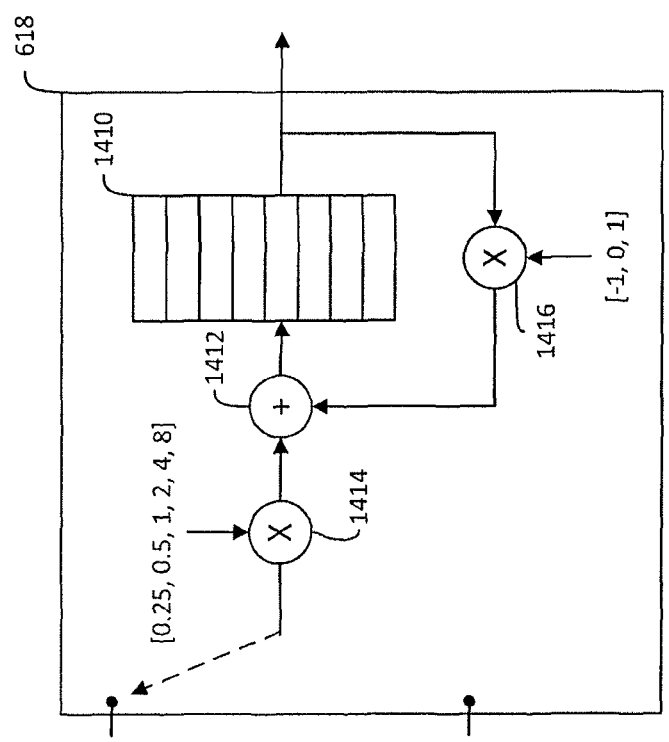
FIG. 14 shows an illustrative architecture for an arithmetic logic unit that may provide data reduction in accordance with some embodiments of the present disclosure.

Additional data compression may be achieved in some embodiments by an integrated optimized arithmetic processing circuit. FIG. 14 shows an illustrative architecture for an arithmetic logic unit (ALU) 618 that may be included as a portion of digital processing block 514. ALU 618 may be configured to perform arithmetic processing of a digital signal to provide data compression. In the illustrative architecture of FIG. 14, ALU 618 includes a sample memory 1410 and digital circuit components such as adder 1412 and multipliers 1414, 1416, that may be used to perform one or more digital signal processing operations including, but not limited to, extending a word size, bit shifting, and accumulating. It should be appreciated that some implementations of ALU 618 may be configured to allow for flexibility for buffer saturation (e.g., clipping), wrapping, or sign extension. In some embodiments, ALU 618 may be configured to operate on the output of each channel in a module, as described above. Alternatively, ALU 618 may be configured to operate on the output of multiple channels in a module to, for example, perform a digital column sum. Arithmetic operations performed by ALU 618 in accordance with some embodiments of the present disclosure may be used to provide one or more of the following: data reduction, increase of signal to noise ratio, cancellation mode imaging, and harmonic imaging. In some embodiments, ALU 618 may alternatively be provided off-chip rather than being integrated on-chip.

Illustrative Image Reconstruction Compression Architectures

Some embodiments in accordance with the present disclosure include on-chip and/or off-chip circuitry for performing at least a portion of an image reconstruction process from digital representations of output from a plurality of integrated ultrasonic transducers. For example, as shown in FIG. 1B, signal conditioning/processing circuit 110 may include image reconstruction circuitry 134 configured to receive a stream of data from MUX 142 or other suitable circuitry components for selecting channel-specific data corresponding to the outputs of the plurality of RX control circuits 106. As discussed in more detail below, image reconstruction circuitry 134 may include on-chip (or off-chip) architectures for performing at least a portion of an image reconstruction process. By performing all or a portion of an image reconstruction process on-chip, an amount of data needed to be transferred off-chip may be significantly reduced, while still providing for reconstruction of images of an acceptable quality for a particular imaging application. Additionally, in some embodiments, output from the at least a portion of the image reconstruction process may be further compressed prior to being transferred off-chip. For example, as shown in FIG. 1B, signal conditioning and processing circuit 110 includes post-processing compression circuitry 136 that compresses the output of at least a portion of an image reconstruction process using image reconstruction circuitry 134. Post-processing compression circuitry 136 may include, for example, circuitry for outputting, for example, at least a portion of a reconstructed image at a desired (e.g., lower) resolution, and the output resolution may be selected based, at least in part, on one or more display and/or processing characteristics of an external device connected to the ultrasound imager 100. Alternatively, the output resolution may be selected using any other suitable criteria.

An example of an illustrative technique for performing at least a portion of an on-chip image reconstruction process involves using beamforming, which can be used to form 2D and/or 3D images. One feature of on-chip beamforming architectures is that a 3D image may be formed in a separable manner where one direction of the image is beamformed and another orthogonal direction is subsequently beamformed. For example, 3D beamforming may be accomplished with two 2D beamforming stages, where none, one, or both of the 2D beamforming steps is performed on-chip. The beamforming architectures described in more detail below also accommodate 2D beamforming in cases where the beam is focused in elevation on transmit and/or receive.

Integrated backprojection is a technique by which acoustic pressure signals are projected back to isotemporal curves based on the time of flight to produce at least a portion of an image. In an example backprojection algorithm, an ultrasound wave having a well-defined wavefront is assumed, so that the time relative to an arbitrary start time at which the wavefront passes through a point in the target scene can be determined. For any point, the time at which a spherical wave originating from a point will take to pass through a receiver may also be determined. The time it takes for a wave scattered by the point to reach the receiver can then be calculated.

Assuming that an ultrasound wave having a well-defined wavefront has been excited, the time $\tau_{tx}(r)$, relative to an arbitrary start time, at which the wavefront passes through a point $r=(x, z)^T$ in the target scene can be calculated. For any point, the time $\tau_{tx}(r, r_k)$ at which a spherical wave originating from a point at r will take to pass through receiver $k=0, \ldots, N-1$ positioned at $r_k$ can also be calculated. The time it takes for a wave scattered by a point r to reach receiver k, is then:

$$\tau(r, r_k) = \tau_{tx}(r) + \tau_{tx}(r, r_k). \quad (1)$$

Each receiver will digitize the waves scattered by the entire scene and produce a signal channel $x_k(t)$. This signal is assumed to be a complex RF signal (e.g., complex analytic). The fundamental concept behind back-projection is to project the data $x_k(t)$ from each point r to all locations in the target scene that could have produced a scattered wave that would coincide with receiver k at time t, given the excitation parameters. This is typically implemented by computing for each receiver k, the sample $x_k(\tau(r, r_k))$ for each corresponding point r by performing a weighted sum of these values over each channel as:

$$y(r) = \sum_{k=0}^{N-1} a(r, r_k) x_k(\tau(r, r_k)). \quad (2)$$

The function a $(r, r_k)$ is known as the spatial apodization function and is optionally used. According to one example of a digital implementation, both space and time are discretized: $r_{ij}=(i\Delta x, j\Delta z)$ and $t_n=nT$, where $\Delta x$, $\Delta z$, and T are the lateral spacing, range spacing, and RF sampling periods, respectively. The spatial discretization implies that there are a finite number of points to compute ($N_x \times N_z$) for the image y[i,j], and the discretization in time implies that interpolation should be performed to extract the values $x_k$ (ti from the discrete signals $x_k$ [m].

Each receiver digitizes the waves scattered by the entire scene and produce a signal channel. This signal may be assumed to be a complex RF signal (i.e., complex analytic). The fundamental concept behind back-projection is to project the data from each point to all locations in the target scene that could have produced a scattered wave that would coincide with a receiver at particular time, given the excitation parameters. This may be implemented by computing, for each receiver channel, the corresponding time sample in the measured signal for each point in the image and performing a weighted sum of these values over each channel.

Backprojection relies on the coherent summation of received waveforms. Critical to this coherency is the proper temporal alignment of the received waveforms. Since sampled signals are used for image reconstruction, the ability to use discrete shifts to properly align the signals is limited. When the sampled data is minimally oversampled, it is often necessary to use fractional sample delays realized by the interpolation of the receive waveform to achieve high-quality backprojected images.

One efficient way to realize a high-speed backprojection algorithm in digital circuitry is to parallelize the computation across channels, so that each RF channel independently and/or simultaneously backprojects its data to an image domain or intermediate domain.

One illustrative technique designed in the architecture is to exploit a shift-invariance on time-of-flight (TOF) and/or apodization for memory re-use. This is because the interpolation indices, based on TOF, depend on the relative position of the transducer and each image point. Therefore, in one embodiment, the receiver TOF and/or receive apodization values may be re-used for subsequent computations within a scan. Similarly, the transmit TOF and/or transmit apodization values may be reused within consecutive scans, for example, when values exhibit shift-invariance. Optionally, the apodization may be restricted, simplifying or eliminating the need for a multiplier circuit and memory, e.g., restricted to 0's and 1's.

Illustrative architectures for image processing may also make use of any number of intermediate buffers, which represent images before compounding them. Another non-limiting technique that may be used with embodiments of the present disclosure is the reuse of image buffer memory when calculating the image, reducing or eliminating the need for intermediate buffers.

Two non-limiting example architectures for realizing such a high-speed back-projection algorithm are described herein. One distributes the same receive time-of-flight information to all channels simultaneously; the other shifts the receive time-of-flight information from element-to-element sequentially. Examples of both of these architectures are described in more detail below.

Figure 15:
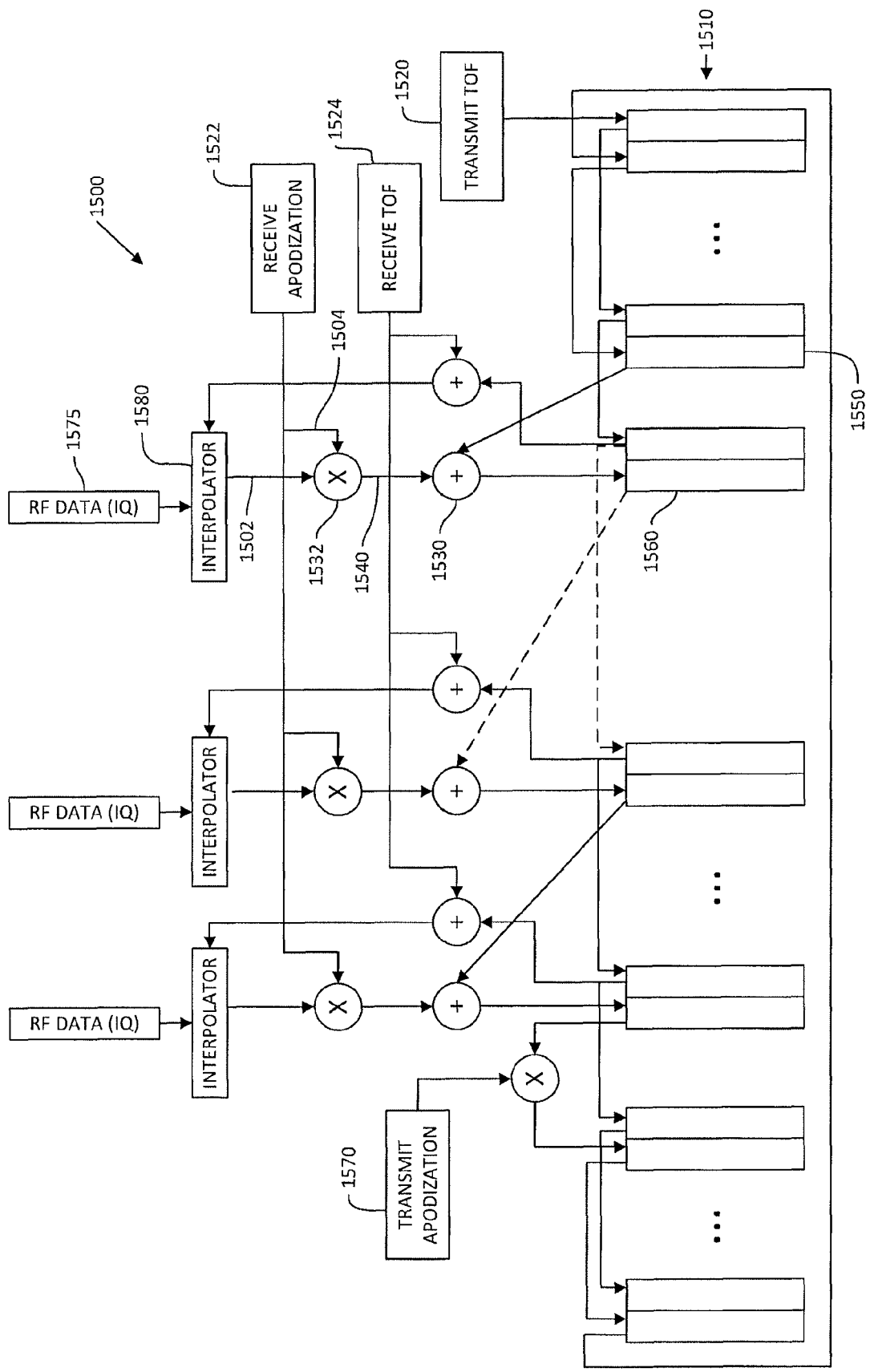
FIG. 15 shows an illustrative architecture for image formation using an integrated backprojection technique in accordance with some embodiments of the present disclosure.

FIG. 15 shows an illustrative architecture 1500 for implementing a back-projection algorithm in accordance with some embodiments of the present disclosure. In this illustrated embodiment, the buffers 1510 are implemented as independent memories. Arrows going into the buffers are connected to the write port, and arrows leaving the buffers are coming from the read port.

For simplicity, it is assumed that the address read is the same as the address written. It should be appreciated, however, that this does not necessarily need to be the case (e.g., often one or more register delays are required, effecting a register delay between address and read). In certain implementations, for example, the data written could be offset from the data read resulting in a circular shift of the data in the buffer. Alternatively, the memory could be clocked at a higher rate than the processing so that reads and writes can happen on different clock cycles.

The backprojection algorithm is implemented by sequentially computing an inner loop for each depth index in the buffer and an outer loop for each iteration index. The number of iterations can be proportional to the number of buffers used, however, it should be appreciated that the number of iterations may be reduced by considering the spatial support of the receive apodization.

One non-limiting example of sequencing may be as follows: (1) The transmit TOF is loaded from the Transmit TOF memory 1520 down to a memory block, (2) For each inner loop cycle, a single address counter controls the read/write locations of all buffers, as well as the apodization 1522, receive TOF 1524, and transmit TOF 1520 memories. The receive TOF values and apodization values can be shared among all subsystems. It should be noted that TOF values and/or apodization values may equivalently be computed during operation as opposed to pre-computed and stored in memory.

The core of the algorithm is implemented by the adder and multiplier in each subsystem (e.g., adder 1530 and multiplier 1532). RF data (IQ) 1575 is received as input. The multiplier (e.g., multiplier 1532) takes in the interpolated signal value 1502 provided from interpolator 1580 and receive apodization value 1504 and produces an apodized signal 1540, which the adder (e.g., adder 1530) then combines with the previous buffer value from the subsystem immediately to the right (e.g., buffer 1550) and writes the combined value into its corresponding buffer (e.g., buffer 1560).

The transmit TOF block 1520, meanwhile, is continually loading in the remaining transmit TOF values. At a particular time, the last transmit TOF value relevant for the current frame will have been written into a buffer. After this time, transmit TOF values for the next excitation begin loading into the transmit TOF buffers. Both the image buffer values and the transmit TOF values are read and shifted to the left subsystem, and can be shifted in a separate set of buffers in the same way as the image values are shifted. Alternatively, the image buffer values and the transmit TOF values can be bitwise concatenated and stored in the same memory, thereby simplifying the layout and design.

The transmit apodization 1570 is multiplied onto the image columns as each column passes by the final element in the transducer. At this point the magnitude of the complex, reconstructed data may be determined thereby reducing the data stored by a factor of two.

After forming one frame (e.g., a single 2D image of a 3D reconstruction), the image can be extracted and presented for display or further processing. However, if the process is continued without extracting the waveform or resetting the buffers, a coherent compounding of the next acquisition onto the current image will begin. If this is desired, or acceptable, then a large savings can be made by waiting until all excitations needed for a complete frame are finished before extraction and reset of the buffers.

The approach outlined above has several advantages. For example, it does not use any large multiplexers and the amount of time taken to form an image is a function of the number of pixels/voxels in that image/volume only.

Figure 16:
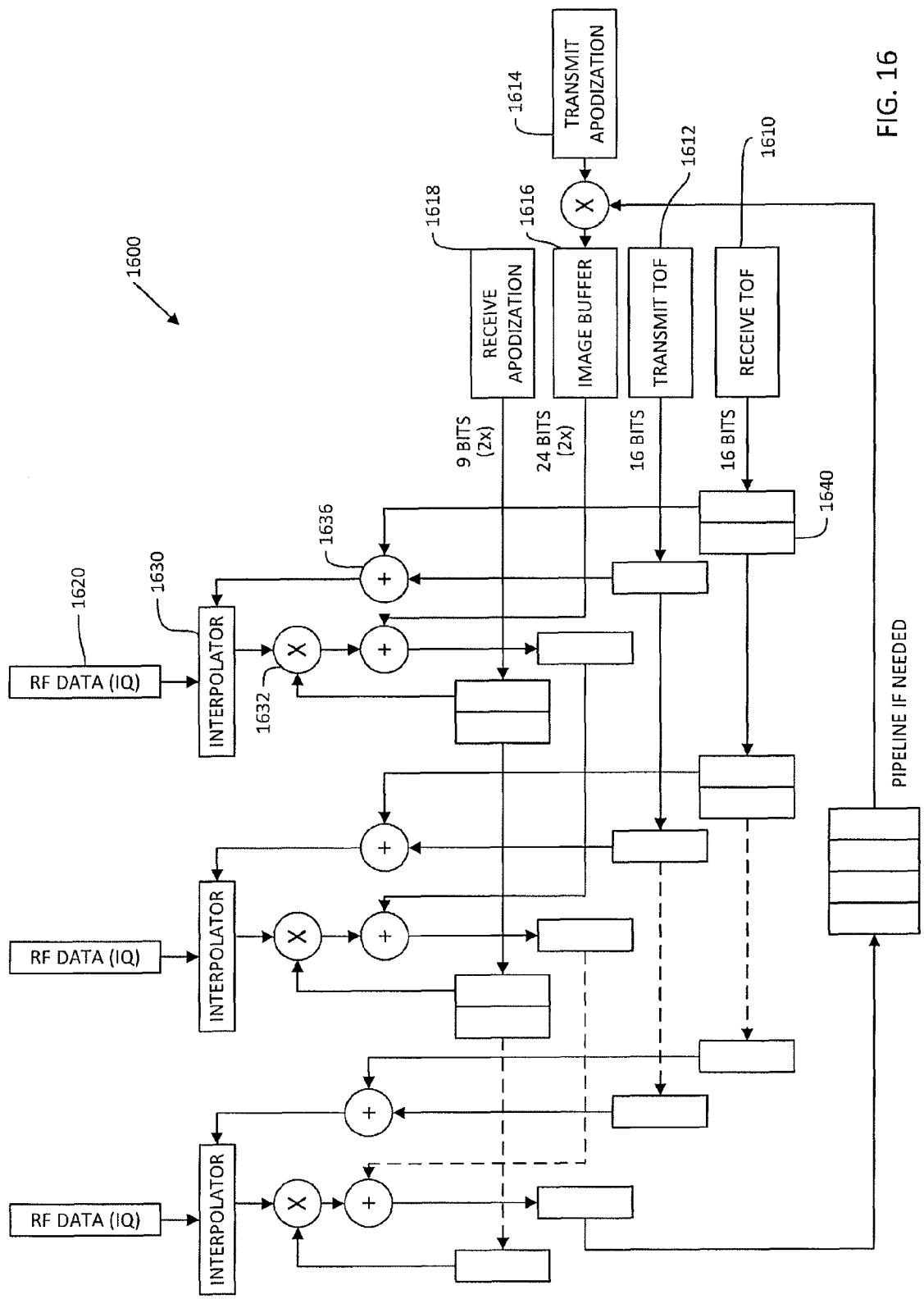
FIG. 16 shows an alternative architecture for image formation using an integrated backprojection technique in accordance with some embodiments of the present disclosure.

FIG. 16 shows an alternative architecture 1600 for implementing a back-projection algorithm in accordance with some embodiments of the present disclosure. As shown, back-projection architecture 1600 receives RF data (IQ) 1620 as input and includes interpolator elements 1630, multiplier elements 1632, adder elements 1636, and buffer elements 1616 and 1640. In some embodiments, one or more of buffer elements 1640 (e.g., the receive apodization buffers) may have a variable amount of buffer elements to allow a finer imaging grid. The illustrative architecture 1600 also includes input buffers for transmit apodization values 1614 and receive apodization values 1618. In this illustrated embodiment, rather than distributing a single receive time-of-flight value to all elements simultaneously, the receive time-of-flight information 1610 is shifted across the array in the same manner as the transmit time-of-flight information 1612 but at half the rate. It should be appreciated that the receive TOF may be alternatively be implemented such that values may be shifted in any rate or direction with adequate buffers to yield similar results. The rate change may be accomplished with an additional buffer between each element, as shown.

The (2N−1) receive TOF buffers may be initialized according to:

$$R_n[j] = \begin{cases} \tau_{rx}[n, j], & 0 \leq n < N \\ \tau_{rx}[2N-1-n, j], & N \leq n < 2N-1 \end{cases}$$

The N transmit TOF buffers may be initialized according to:

$$T_n[j] = \begin{cases} \tau_{tx}[0, j], & n = 0 \\ \tau_{tx}[N-n, j], & 1 \leq n < 2N \end{cases}$$

An example loading scheme for receive parameters is illustrated in the table below:

| Iteration | Element 0 | | | Element 1 | | | Element 2 | | | Element 3 | | |
|---|---|---|---|---|---|---|---|---|---|---|---|---|
| 1 | $R_1[j]$ | | | $R_2[j]$ | $R_3[j]$ | | $R_3[j]$ | $R_2[j]$ | | $R_1[j]$ | | $R_0[j]$ |
| 2 | $R_2[j]$ | | | $R_3[j]$ | $R_3[j]$ | | $R_2[j]$ | $R_1[j]$ | | $R_0[j]$ | | $R_1[j]$ |
| 3 | $R_3[j]$ | | | $R_3[j]$ | $R_2[j]$ | | $R_1[j]$ | $R_0[j]$ | | $R_1[j]$ | | $R_2[j]$ |
| 4 | $R_3[j]$ | | | $R_2[j]$ | $R_1[j]$ | | $R_0[j]$ | $R_1[j]$ | | $R_2[j]$ | | $R_3[j]$ |
| 5 | $R_2[j]$ | | | $R_1[j]$ | $R_0[j]$ | | $R_1[j]$ | $R_2[j]$ | | $R_3[j]$ | | $R_3[j]$ |
| 6 | $R_1[j]$ | | | $R_0[j]$ | $R_1[j]$ | | $R_2[j]$ | $R_3[j]$ | | $R_3[j]$ | | $R_2[j]$ |
| 7 | $R_0[j]$ | | | $R_1[j]$ | $R_2[j]$ | | $R_3[j]$ | $R_3[j]$ | | $R_4[j]$ | | $R_1[j]$ |

The legend for the shading in the table above is as follows:

| Column 0 | Column 1 | Column 2 | Column 3 |

An example loading scheme for transmit parameters is illustrated in the table below:

| Iteration | Element 0 | Element 1 | Element 2 | Element 3 |
|---|---|---|---|---|
| 1 | $T_1[j]$ | $T_2[j]$ | $T_3[j]$ | $T_0[j]$ |
| 2 | $T_2[j]$ | $T_3[j]$ | $T_0[j]$ | $T_1[j]$ |
| 3 | $T_3[j]$ | $T_0[j]$ | $T_1[j]$ | $T_2[j]$ |
| 4 | $T_0[j]$ | $T_1[j]$ | $T_2[j]$ | $T_3[j]$ |
| 5 | $T_1[j]$ | $T_2[j]$ | $T_3[j]$ | $T_0[j]$ |
| 6 | $T_2[j]$ | $T_3[j]$ | $T_0[j]$ | $T_1[j]$ |
| 7 | $T_3[j]$ | $T_0[j]$ | $T_1[j]$ | $T_2[j]$ |

The illustrative back-projection architectures described above are described with respect to a two-dimensional image reconstruction processor. The architecture may be extended to three-dimensions by using a tomographic approach (i.e., building the third dimension as slices), or by using any other suitable technique.

Some embodiments may be configured to employ Doppler imaging, which compresses data using ensemble compression. Doppler processing attempts to measure velocities in tissue by observing phase shifts in multiple echoes across time. A Doppler imaging sequence consists of multiple data acquisition frames termed an ensemble. The length of a Doppler ensemble (also called packet size) is typically 8 to 16 frames.

The signal from a single point of interest can be represented as $S(t) = A_1 e^{i\Phi_0} + A_2 e^{i\Phi_1(t)}$, where $S(t)$ is the point of interest in the reconstructed images as a function of time, the $A_1$ term represents background scattering from immobile tissue source, and the $A_2$ term represents the changing signal due to a moving scatterer. A challenge with Doppler processing is due to the magnitude of the difference between $A_1$ and $A_2$. The magnitude of the difference depends on the imaged tissue. For example, in the kidney, $A_1$ may be up to 40 dB larger than $A_2$ due to the small size of the vessels containing the flowing blood; the echo signals simultaneously contain both tissue and blood scattering. In the carotid artery the difference between $A_1$ and $A_2$ is far smaller. For example, the $A_1$ term may be zero in certain areas as the large vessel allows the complete isolation of blood backscatter and tissue backscatter. Isolating $A_2$ from $A_1$ requires a wall filter (also referred to as a clutter filter) and is described in more detail below.

Multiple acquisitions of data provide ensembles for Doppler processing at a designated pulse repetition frequency (PRF). From this set of ensembles, velocities can be calculated. Often a wall filter is implemented to remove the non-moving scene scatterers, where the data has first been beamformed. This wall filter may be implemented, for example, with a Finite Impulse Response (FIR) filter or a matrix multiply across the ensembles. Other options for a wall filter include, but are not limited to, an Infinite Impulse Response (IIR) and a filter via Fast Fourier Transform (FFT). The beamformed image for an ensemble of $m = 0 \ldots M-1$ images is given by $Y = y(r, m)$. The wall filtered data is given by:

$$Y_w = YW$$

$$y_w(r, n) = \sum_{m=0}^{M-1} y(r, m) w(m, n)$$

where w(m,n) is the wall filter, a M×N, 2D matrix with M filter values is used to remove the low frequencies, and $N_t$ filters are used to calculate autocorrelation values. In the simplest case, $N_t$=M, though it should be appreciated that other values of $N_t$ may alternatively be used. When designing and implementing a wall filter, one should be mindful of whether the filter response is a square or non-square matrix.

After the wall filter, an autocorrelation function can be used to find the power of the flow and/or the direction of the flow. A lag-0 autocorrelation provides a power calculation and a lag-1 autocorrelation provides a flow calculation. (Note: lag-1 autocorrelation may provide sufficient power and color flow Doppler). The lag-1 autocorrelation is given by:

$$R_1(r,\tau) = y_w(r,\tau+1) y_w^*(r,\tau), \text{ where } z = 1 \ldots N_t - 1$$

If it is assumed that $y_w(r,\tau) = s(r) e^{i\phi\tau}$, where $e^{i\phi\tau}$ represents the phase change due to motion between frames, the phase of the lag-1 correlation values is equal to 0.

$$R_1(r,\tau) = y_w(r,\tau+1) y_w^*(r,\tau)$$

$$R_1(r,\tau) s(r) e^{i\phi(\tau+1)} s^*(r) e^{-i\phi\tau}$$

$$R_1(r,\tau) = |s(r)|^2 e^{i\phi}$$

Finally the average value of the lag-1 autocorrelation provides an estimate of velocity (or power for lag-0) for each point r. The mean value is calculated by first taking the sum and then dividing by $N_t - 1$. The Doppler signal is thus given by:

$$D(r) = \frac{1}{N_t - 1} \sum_{k=0}^{N_t - 2} R_1(r, k)$$

In a digital implementation, space is discretized: $r_{ij} = (i\Delta x, j\Delta z)$, where $\Delta x$, $\Delta z$ are the lateral spacing and range spacing, respectively. The spatial discretization implies that there are a finite number of points to compute ($N_x \times N_z$) for the backscatter image y[i, j] and Doppler image D[i, j].

Figure 17:
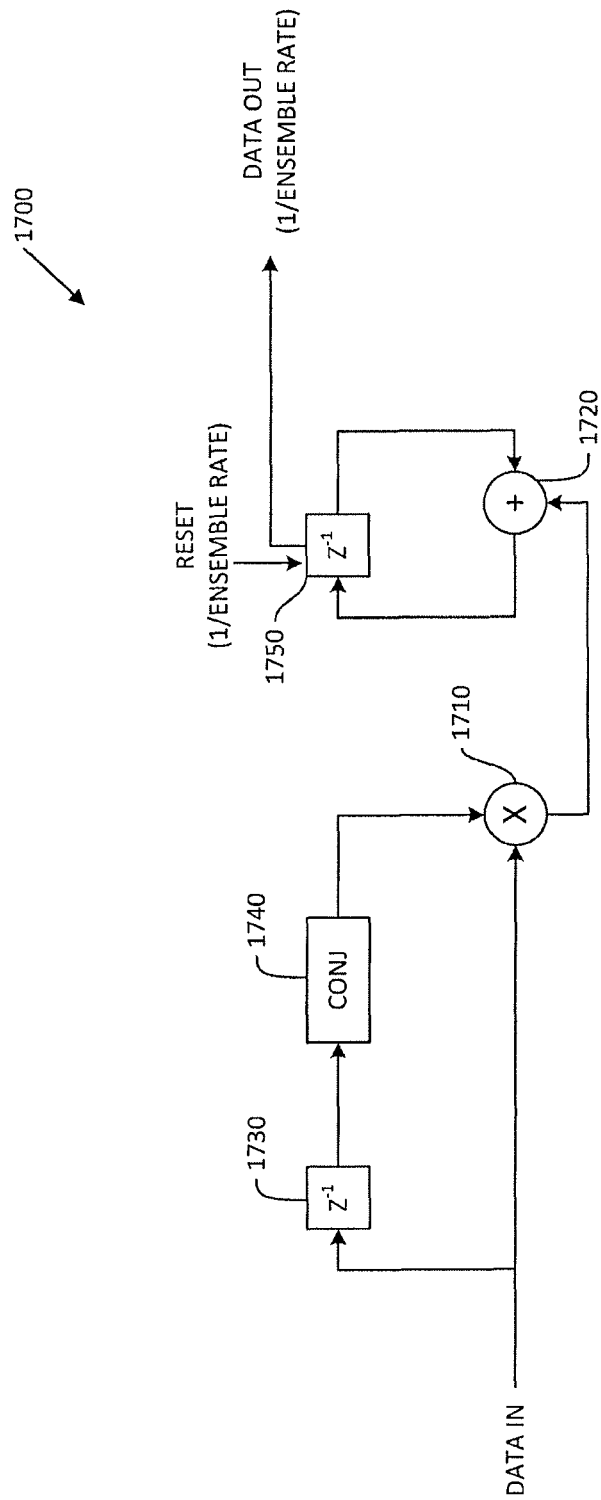
FIG. 17 shows an illustrative architecture for performing ensemble compression in accordance with some embodiments of the present disclosure.

FIG. 17 shows an illustrative architecture 1700 for performing Doppler imaging using ensemble compression in accordance with some embodiments of the present disclosure. In the illustrated architecture the hardware of a backprojection architecture (e.g., backprojection architectures shown in FIGS. 15 and 16) is used to perform the wall filter for all ensembles. After this, when the data is provided off-chip using a data stream, a register 1750 and an adder 1720 (which together make an accumulator) and a complex multiplier 1710 are used to calculate the lag-1 autocorrelation and finally the Doppler values. As shown, Doppler imaging architecture 1700 also includes delay element 1730 and complex conjugate element 1740.

Backprojection architectures allow for matrix multiplication with appropriate order of operations and reuse of memory. As an example, the Doppler wall filtering matrix multiply may be accomplished within the backprojection architecture by storing the matrix coefficients within the receive apodization memory and storing the ordered indices in the receive TOF memory (see table below for example orders). In this instance, the receive TOF values repeat the same index consecutively into the RF buffer for the number of ensembles. In particular, the values in the receive apodization buffer include values of the wall filter matrix to be multiplied with each ensemble value. Once the wall filter values have been multiplied for a single excitation, the buffer values pass unchanged through the backprojection pipeline. The buffer values are fed back such that the remaining values of the ensemble are multiplied by the next coefficients of the wall filter. This process is repeated until the matrix multiply is complete. For the Doppler calculations, another processing unit may be used to process the data as the computed values exit the buffer. An example of this processing unit is seen in architecture 1700 and performs the operations described in the equations above to calculate the values in D[i,j]. The data is loaded into a register and multiplied such that an autocorrelation of lag-1 is computed and results are summed over the number of ensembles collected (minus 1 for the lag difference). Note that any number of registers 1730 may be used or multiplexed to form any desirable lag autocorrelation.

|     | Col | | | |
| --- | --- | --- | --- | --- |
| Row | 0 | 1 | ... 14 | 15 |
| 0 | $y(r_{(0, 0)}, 0)w(0, 0)$ | $y(r_{(0, 1)}, 0)w(0, 0)$ | ... $y(r_{(0, 14)}, 0)w(0, 0)$ | $y(r_{(0, 15)}, 0)w(0, 0)$ |
| 1 | $y(r_{(0, 0)}, 0)w(0, 1)$ | $y(r_{(0, 1)}, 0)w(0, 1)$ | ... $y(r_{(0, 14)}, 0)w(0, 1)$ | $y(r_{(0, 15)}, 0)w(0, 0)$ |
| . | | | ... | |
| 6 | $y(r_{(0, 0)}, 0)w(0, 6)$ | $y(r_{(0, 1)}, 0)w(0, 6)$ | ... $y(r_{(0, 14)}, 0)w(0, 6)$ | $y(r_{(0, 15)}, 0)w(0, 6)$ |
| 7 | $y(r_{(0, 0)}, 0)w(0, 7)$ | $y(r_{(0, 1)}, 0)w(0, 7)$ | ... $y(r_{(0, 14)}, 0)w(0, 7)$ | $y(r_{(0, 15)}, 0)w(0, 7)$ |
| 8 | $y(r_{(1, 0)}, 0)w(0, 0)$ | $y(r_{(1, 1)}, 0)w(0, 0)$ | ... $y(r_{(1, 14)}, 0)w(0, 0)$ | $y(r_{(1, 15)}, 0)w(0, 0)$ |
| 9 | $y(r_{(1, 0)}, 0)w(0, 1)$ | $y(r_{(1, 1)}, 0)w(0, 1)$ | ... $y(r_{(1, 14)}, 0)w(0, 1)$ | $y(r_{(1, 15)}, 0)w(0, 0)$ |
| . | | | ... | |
| 14 | $y(r_{(1, 0)}, 0)w(0, 6)$ | $y(r_{(1, 1)}, 0)w(0, 6)$ | ... $y(r_{(1, 14)}, 0)w(0, 6)$ | $y(r_{(1, 15)}, 0)w(0, 6)$ |
| 15 | $y(r_{(1, 0)}, 0)w(0, 7)$ | $y(r_{(1, 1)}, 0)w(0, 7)$ | ... $y(r_{(1, 14)}, 0)w(0, 7)$ | $y(r_{(1, 15)}, 0)w(0, 7)$ |
| . | | | ... | |
| 504 | $y(r_{(63, 0)}, 0)w(0, 0)$ | $y(r_{(63, 1)}, 0)w(0, 0)$ | ... $y(r_{(63, 14)}, 0)w(0, 0)$ | $y(r_{(63, 15)}, 0)w(0, 0)$ |
| 505 | $y(r_{(63, 0)}, 0)w(0, 1)$ | $y(r_{(63, 1)}, 0)w(0, 1)$ | ... $y(r_{(63, 14)}, 0)w(0, 1)$ | $y(r_{(63, 15)}, 0)w(0, 0)$ |
| . | | | ... | |
| 510 | $y(r_{(63, 0)}, 0)w(0, 6)$ | $y(r_{(63, 1)}, 0)w(0, 6)$ | ... $y(r_{(63, 14)}, 0)w(0, 6)$ | $y(r_{(63, 15)}, 0)w(0, 6)$ |
| 511 | $y(r_{(63, 0)}, 0)w(0, 7)$ | $y(r_{(63, 1)}, 0)w(0, 7)$ | ... $y(r_{(63, 14)}, 0)w(0, 7)$ | $y(r_{(63, 15)}, 0)w(0, 7)$ |

Other image reconstruction techniques including, but not limited to, Fourier resampling and shearwave processing are also contemplated for use with some embodiments of the present disclosure.

FIGS. 18A and 18B show illustrative dynamic focus architectures that may be used in accordance with some embodiments of the present disclosure. The dynamic focus architectures perform a dynamic delay-and-sum operation over a single excitation. A dynamic focus beamformer may delay the return signals from an acoustic field so that the scatterings from equal times along a line (or plane) are summed between all receive transducer element. In some embodiments, this is done in a streaming architecture that does not need to store all of the data for a single acquisition in memory. FIG. 18A shows an illustrative architecture 1800 for implementing dynamic focusing when streaming addressable delays are used. Architecture 1800 includes upsampling element 1802, which receives ADC data at a sampling rate of $f_s$, register 1804 (e.g., a 1024 value 10-bit addressable shift register), multiplier 1806, and adder 1820. It should be appreciated that any suitable sampling rate $f_s$ (e.g., 200 MHz, 100 MHz, 50 MHz, etc.) may be used in the architecture 1800. Additionally, any suitable size buffers or registers may be used. FIG. 18B shows an illustrative architecture 1810 for implementing dynamic focusing when pipeline delays are used. Architecture 1810 includes register 1804, which receives ADC data at a sampling rate $f_s$, upsampling element 1802, downsampling element 1808, multiplier 1806, and integrator 1820. It should be appreciated that any suitable sampling rate $f_s$ (e.g., 200 MHz, 100 MHz, 50 MHz, etc.) may be used in the architecture 1810. Additionally, any suitable size buffers or registers may be used.

Direct compounding is a data reduction technique where multiple excitations are collected and added together as an intermediate stage toward image reconstruction. When an ultrasonic excitation wavefield is shift-invariant, e.g., the field pressures are identically shifted for each point in space, then the excitation is considered spatially-invariant. Compounding a spatially-invariant excitation allows for reduced data rates with a reduced quality penalty in the reconstruction. One implementation uses a number of virtual sources, which may be only slightly more than the number of plane waves one would have sent for high quality images. On-chip additions in the ADC buffer may provide an ability to compress the data upon collection. Data resulting from various excitations including, but not limited to, virtual source, focused beams, plane waves and several other spatially invariant beams may be compounded prior to image reconstruction.

Figure 19:
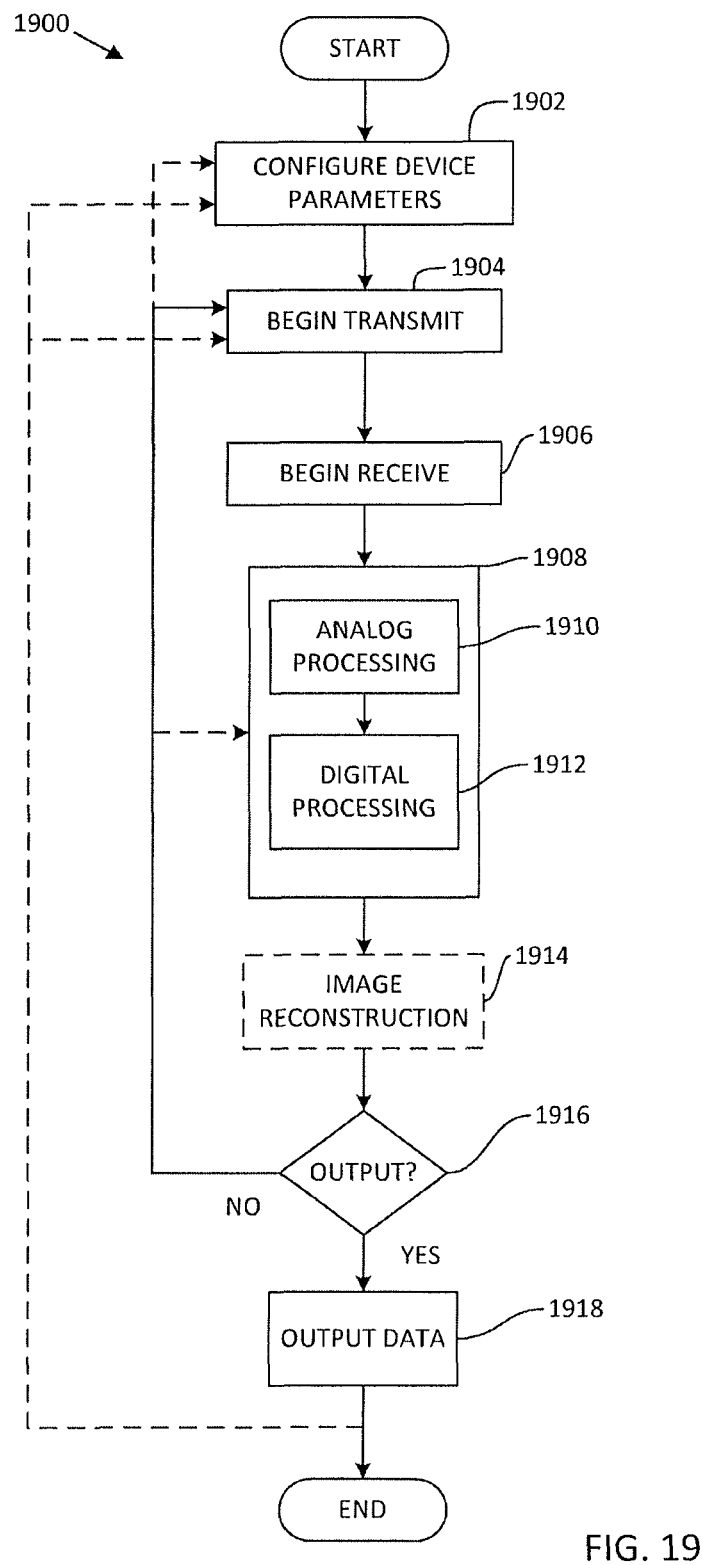
FIG. 19 is a flowchart of an illustrative process for operating an ultrasonic transducer array, in accordance with some embodiments of the present disclosure.

Aspects of operation of the circuitry described herein are further explained below with reference to FIG. 19, which is a flowchart of an illustrative process 1900 for operating an ultrasound data device in accordance with some embodiments that incorporate data reduction circuitry. Process 1900 may be performed, in whole or in part, by any suitable ultrasound device (e.g., ultrasound device 100 described with reference to FIG. 1B and FIG. 3).

Process 1900 begins at stage 1902, where one or more parameters of the ultrasound device are configured. The parameters may be configured in any suitable way, and embodiments are not limited in this respect. For example, in some embodiments, configuring the one or more parameters of the ultrasound device includes loading transmit and/or receive parameters into control registers that provide information to the device for controlling its operation. In some embodiments, configuring the one or more parameters includes accessing the parameters stored in memory on the device based on a selected or programmed imaging mode of operation, as discussed above. Additionally, any suitable parameters may be configured in stage 1902 including, but not limited to, transmit parameters, receive chain compression parameters, and sequence timing parameters.

After the parameter(s) for the ultrasound device have been configured, the process 1900 proceeds to stage 1904, where the ultrasound device begins transmitting. For example, one or more components of the ultrasound device may access transmit parameters loaded into registers on the device (e.g., the transmit parameters configured in stage 1902) and based, at least in part, on these parameters, elements of the ultrasound transducer array may be instructed to transmit acoustic energy.

The process 1900 then proceeds to stage 1906, where the elements of the ultrasound transducer array begin receiving data in response to the transmitted acoustic energy. The process 1900 then proceeds to stage 1908, where the received data is processed by analog and/or digital components of the receive signal processing chain described above. In some embodiments, data compression is performed on the received data in real-time as data is being received from the ultrasound transducer array. In other embodiments, at least some of the received data is stored in on-chip memory prior to being compressed, and embodiments of the present disclosure are not limited in this respect.

As shown in stage 1910, and as described above, at least some processing of the received signals may include subjecting the signals to analog processing by analog signal processing electronics including, but not limited to, the analog signal processing architectures described above (e.g., filtering, averaging, variable gain amplification controlled by a time gain compensation circuit, etc.). In some embodiments, the output of the analog signal processing chain is provided to an analog-to-digital converter to convert the processed analog data signals to a digital representation, as discussed above.

Following analog processing and analog-to-digital conversion, the process 1900 proceeds to stage 1912, where the digital signal(s) are compressed using one or more digital compression architectures including, but not limited to those architectures discussed above for demodulation, filtering, decimation, re-quantization, and arithmetic processing.

Following signal processing for data compression, the process 1900 proceeds to stage 1914, where the digitally-processed signals are optionally used to perform at least a portion of an image reconstruction process. As discussed above, in some embodiments, at least a portion of an image reconstruction process based on the received data may be performed using image reconstruction components formed on a same substrate as the ultrasound transducer array. In other embodiments, the compressed signal is transmitted off-chip for image reconstruction processing using, for example, an FPGA or other processing circuit(s). In some embodiments, a portion of an image reconstruction process is performed on-chip to provide data compression prior to transmitting the data off-chip.

Regardless of whether a portion of an image reconstruction process has been performed on-chip, off-chip, or partially on-chip and partially off-chip, the process 1900 proceeds to stage 1916, where it is determined whether to output the data off-chip or to begin another excitation (e.g., with the intention of processing the previous excitation with the next, e.g., for Doppler processing, harmonic imaging enhancement, averaging, or other appropriate processing). If it is determined in stage 1916 to output the data, the process 1900 proceeds to stage 1918, where the data is transmitted to an external device as a data stream. As discussed above, the output interface connected to the external device may be bandwidth limited, and the architectures described herein may be used to provide data compression sufficient to enable ultrasound imaging-on-a-chip to be realized, while also being able to transmit the data off-chip at a rate supported by the output interface.

After the data is output in stage 1918, the process 1900 may optionally return to stage 1902 or stage 1904, where more data can be collected using the ultrasound device using the same or different device parameters. For example, if the process 1900 returns to stage 1902, all or a subset (i.e., less than all) of the device parameters may be configured prior to transmission of new excitations from the ultrasound transducer array. Alternatively, if the process 1900 returns to stage 1904, the transmission circuitry may be instructed to send another excitation without modifying the device parameters.

If it is determined in stage 1916 that the data should not be output, the process 1900 returns to one or more of stages 1902, 1904, or 1908, depending for example, on the imaging mode of the ultrasound device. In embodiments where at least a portion of an image reconstruction process is performed on-chip, the process may return to stage 1902, where the transmission circuitry is instructed to send excitations based on different parameters to enable compounding image data on chip. For example, in harmonic imaging, the ALU parameters may be adjusted in stage 1902. For averaging or Doppler processing, the process may return to stage 1904, where the transmission circuitry is instructed to send another excitation without modifying the parameters. In yet other embodiments, the process returns to stage 1908 to perform additional processing prior to outputting the signals off-chip. The process 1900 continues until it is determined in stage 1918 to output the data off-chip. It should be appreciated that process 1900 is illustrative and that variations are contemplated.

In some embodiments, memory used to achieve some or all of the above-described functionality may be located on-chip, i.e., on the die 112. In other embodiments, however, some or all of the memory used to implement some or all of the described functionality may be located off-chip, with the remainder of the circuitry, software, and/or other components being located on the die 112.

Having thus described several aspects and embodiments of the technology set forth in the disclosure, it is to be appreciated that various alterations, modifications, and improvements will readily occur to those skilled in the art. Such alterations, modifications, and improvements are intended to be within the spirit and scope of the technology described herein. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

The above-described embodiments can be implemented in any of numerous ways. One or more aspects and embodiments of the present disclosure involving the performance of processes or methods may utilize program instructions executable by a device (e.g., a computer, a processor, or other device) to perform, or control performance of, the processes or methods. In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement one or more of the various embodiments described above. The computer readable medium or media can be transportable, such that the program or programs stored thereon can be loaded onto one or more different computers or other processors to implement various ones of the aspects described above. In some embodiments, computer readable media may be non-transitory media.

The terms "program" or "software" are used herein in a generic sense to refer to any type of computer code or set of computer-executable instructions that can be employed to program a computer or other processor to implement various aspects as described above. Additionally, it should be appreciated that according to one aspect, one or more computer programs that when executed perform methods of the present disclosure need not reside on a single computer or processor, but may be distributed in a modular fashion among a number of different computers or processors to implement various aspects of the present disclosure.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a Personal Digital Assistant (PDA), a smartphone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible formats.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

What is claimed is:

1. An ultrasound device, comprising:
at least one ultrasonic transducer element integrated on a semiconductor die;
an analog to digital converter (ADC) integrated on the semiconductor die, wherein the ADC is configured to process a signal output from the at least one ultrasonic transducer element to produce a digital signal; and
a compression circuit integrated on the semiconductor die and configured to generate a compressed signal by compressing the digital signal, wherein the compressed signal is configured to be transmitted from the semiconductor die as a data stream, wherein the compression circuit further comprises a filter, a decimation circuit, a re-quantization circuit, and an arithmetic logic unit (ALU), wherein an output of the filter is coupled to an input of the decimation circuit, an output of the decimation circuit is coupled to an input of the re-quantization circuit, and an output of the re-quantization circuit is coupled to an input of the ALU; and
wherein the compression circuit is configured to generate the compressed signal prior to any image reconstruction process.

2. The ultrasound device of claim 1, wherein the compression circuit includes quadrature demodulation circuitry and wherein the compression circuit is configured to compress the digital signal using the quadrature demodulation circuitry.

3. The ultrasound device of claim 1, wherein the compression circuit includes down-sampling circuitry, and wherein the compression circuit is configured to compress the digital signal using the down-sampling circuitry.

4. The ultrasound device of claim 1, wherein the filter includes a cascade integrating comb (CIC) filter, and wherein the compression circuit is configured to compress the digital signal using the CIC filter.

5. The ultrasound device of claim 1, wherein the arithmetic logic unit is configured to perform at least one operation on the digital signal selected from the group consisting of extending a word size, bit shifting, accumulating, and subtracting.

6. The ultrasound device of claim 1, further comprising an output interface configured to output the data stream from the semiconductor die.

7. The ultrasound device of claim 6, wherein the output interface is a high-speed serial interface selected from the group consisting of a USB 3.0 interface, a USB 3.1 interface, a USB 2.0 interface, a Thunderbolt interface, a FireWire interface, and a Gigabit Ethernet interface.

8. The ultrasound device of claim 1, wherein the compression circuit is configured to compress the digital signal based, at least in part, on a mode of operation of the ultrasound device.

9. The ultrasound device of claim 1, further comprising image reconstruction circuitry configured to perform at least a portion of an image reconstruction process based, at least in part, on the compressed signal.

10. The ultrasound device of claim 9, wherein the image reconstruction circuitry is configured to perform at least a portion of an image reconstruction process using a beamforming technique.

11. The ultrasound device of claim 10, wherein the beamforming technique comprises using an integrated back-projection technique, in which at least one of receiver time-of-flight values and receive apodization values are reused within consecutive scans.

12. The ultrasound device of claim 1, further comprising a memory integrated on the semiconductor die, the memory configured to selectively store the digital signal prior to the digital signal being compressed by the compression circuit.

13. A method for processing a signal output from an ultrasonic transducer element, comprising:

with a component integrated on a same semiconductor die as the ultrasonic transducer element, processing the signal output from the ultrasonic transducer element to produce a digital signal; and with at least one additional component integrated on the semiconductor die, producing a compressed signal by compressing the digital signal, wherein the compressed signal is configured to be transmitted from the semiconductor die as a data stream, wherein compressing the digital signal comprises filtering the digital signal with a filter integrated on the semiconductor die to produce a filtered signal, decimating the filtered signal with a decimation circuit integrated on the semiconductor die to produce a decimated signal, re-quantizing the decimated signal with a re-quantization circuit integrated on the semiconductor die to produce a re-quantized signal, and processing the re-quantized signal with an arithmetic logic unit (ALU) integrated on the semiconductor die; and wherein the compressed signal is produced prior to any image reconstruction process.

14. The method of claim 13, wherein compressing the digital signal comprises performing quadrature demodulation on the digital signal.

15. The method of claim 13, wherein compressing the digital signal comprises down-sampling the digital signal.

16. The method of claim 13, wherein filtering the digital signal comprises filtering the digital signal using a cascade integrated comb (CIC) filter integrated on the semiconductor die.

17. The method of claim 13, wherein processing the re-quantized signal using the arithmetic logic unit comprises performing at least one operation on the re-quantized signal selected from the group consisting of extending a word size, bit shifting, accumulating, and subtracting.

18. The method of claim 13, further comprising outputting the data stream from the semiconductor die via an output interface.

19. The method of claim 18, wherein the output interface is a high-speed serial interface selected from the group consisting of a USB 3.0 interface, a USB 3.1 interface, a USB 2.0 interface, a Thunderbolt interface, a FireWire interface, and a Gigabit Ethernet interface.

20. The method of claim 13, wherein compressing the digital signal comprises compressing the digital signal based, at least in part, on a mode of operation of a device including the ultrasonic transducer element.

21. The method of claim 13, further comprising performing at least a portion of an image reconstruction process based, at least in part, on the compressed signal.

22. The method of claim 21, wherein performing at least a portion of an image reconstruction process comprises performing beamforming.

23. The method of claim 22, wherein performing beamforming comprises using an integrated backprojection technique, in which at least one of receiver time-of-flight values and receive apodization values are reused within consecutive scans.

24. The method of claim 13, further comprising selectively storing the digital signal in a memory integrated on the semiconductor die, prior to compressing the digital signal being compressed by the compression circuit.

* * * * *